US008808998B2

(12) United States Patent
Low

(10) Patent No.: US 8,808,998 B2
(45) Date of Patent: *Aug. 19, 2014

(54) DIAGNOSTIC METHOD FOR ATHEROSCLEROSIS

(71) Applicant: Purdue Research Foundation, West Lafayette, IN (US)

(72) Inventor: Philip S. Low, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/714,659

(22) Filed: Dec. 14, 2012

(65) Prior Publication Data

US 2013/0101519 A1    Apr. 25, 2013

Related U.S. Application Data

(60) Continuation of application No. 13/083,121, filed on Apr. 8, 2011, now Pat. No. 8,383,354, which is a division of application No. 11/022,088, filed on Dec. 23, 2004, now Pat. No. 7,977,058, which is a continuation-in-part of application No. PCT/US2004/016667, filed on May 27, 2004.

(60) Provisional application No. 60/474,731, filed on May 30, 2003.

(51) Int. Cl.
G01N 33/53 (2006.01)

(52) U.S. Cl.
USPC .......................................................... 435/7.1

(58) Field of Classification Search
None
See application file for complete search history.

(56) References Cited

U.S. PATENT DOCUMENTS

| | | |
|---|---|---|
| 2,816,110 A | 12/1957 | Sletzinger et al. |
| 4,577,636 A | 3/1986 | Spears |
| 4,641,650 A | 2/1987 | Mok |
| 4,713,249 A | 12/1987 | Schroder |
| 4,718,417 A | 1/1988 | Kittrell et al. |
| 4,785,806 A | 11/1988 | Deckelbaum |
| 4,817,601 A | 4/1989 | Roth et al. |
| 4,850,351 A | 7/1989 | Herman et al. |
| 4,917,084 A | 4/1990 | Sinofsky |
| 4,950,266 A | 8/1990 | Sinofsky |
| 5,094,848 A | 3/1992 | Brixner |
| 5,108,921 A | 4/1992 | Low et al. |
| 5,140,104 A | 8/1992 | Coughlin et al. |
| 5,192,525 A | 3/1993 | Yang et al. |
| 5,217,456 A | 6/1993 | Narciso |
| 5,266,333 A | 11/1993 | Cady et al. |
| 5,275,594 A | 1/1994 | Baker et al. |
| 5,336,506 A | 8/1994 | Josephson et al. |
| 5,373,093 A | 12/1994 | Vallarino et al. |
| 5,399,338 A | 3/1995 | Born et al. |
| 5,416,016 A | 5/1995 | Low et al. |
| 5,417,982 A | 5/1995 | Modi |
| 5,547,668 A | 8/1996 | Kranz et al. |
| 5,552,545 A | 9/1996 | Pearce et al. |
| 5,562,100 A | 10/1996 | Kittrell et al. |
| 5,576,305 A | 11/1996 | Ratcliffe |
| 5,688,488 A | 11/1997 | Low et al. |
| 5,753,631 A | 5/1998 | Paulson et al. |
| 5,759,546 A | 6/1998 | Weinberg et al. |
| 5,820,847 A | 10/1998 | Low et al. |
| 6,093,382 A | 7/2000 | Wedeking et al. |
| 6,167,297 A | 12/2000 | Benaron |
| 6,204,371 B1 | 3/2001 | Levinson |
| 6,217,847 B1 | 4/2001 | Contag et al. |
| 6,221,334 B1 | 4/2001 | Wedeking et al. |
| 6,246,901 B1 | 6/2001 | Benaron |
| 6,270,766 B1 | 8/2001 | Feldman et al. |
| 6,335,434 B1 | 1/2002 | Guzaev et al. |
| 6,365,362 B1 | 4/2002 | Terstappen et al. |
| 6,387,350 B2 | 5/2002 | Goldenberg |
| 6,507,747 B1 | 1/2003 | Gowda et al. |
| 6,780,984 B2 | 8/2004 | Wang et al. |

(Continued)

FOREIGN PATENT DOCUMENTS

| | | |
|---|---|---|
| EP | 1940473 | 7/2008 |
| JP | 2003-515570 | 5/2003 |
| RU | 21 23338 | 11/1996 |
| WO | 90/12096 | 10/1990 |
| WO | 91/19501 | 12/1991 |
| WO | 91/19502 | 12/1991 |
| WO | 96/22521 | 7/1996 |
| WO | 96/36367 | 11/1996 |
| WO | 97/37690 | 10/1997 |
| WO | 01/19320 | 3/2001 |

(Continued)

OTHER PUBLICATIONS

Achilefu et al., "Novel Receptor-Targeted Fluorescent Contrast Agents for In Vivo Tumor Imaging", Investigative Radiology, vol. 35, No. 8, pp. 479-485, Aug. 2000.

(Continued)

*Primary Examiner* — Nora Rooney
(74) *Attorney, Agent, or Firm* — Barnes & Thornburg LLP

(57) ABSTRACT

The invention relates to a method of identifying/monitoring active atherosclerotic plaques associated with blood vessel walls wherein the plaques comprise activated macrophages having accessible binding sites for a ligand. The method comprises the steps of administering to a patient being evaluated for atherosclerosis an effective amount of a composition comprising a conjugate of a ligand and a chromophore capable of emitting light under predetermined conditions, allowing sufficient time for the ligand conjugate to bind to the activated macrophages, subjecting the blood vessels to the predetermined conditions using a catheter-based device, and identifying active plaques by detecting light emitted by the chromophore using a catheter-based device or by using an external imaging technique. The invention also relates to a similar method wherein a chemical moiety capable of emitting radiation is conjugated to the ligand.

32 Claims, 12 Drawing Sheets
(3 of 12 Drawing Sheet(s) Filed in Color)

(56) References Cited

U.S. PATENT DOCUMENTS

| | | |
|---|---|---|
| 6,782,289 B1 | 8/2004 | Strauss |
| 6,960,449 B2 | 11/2005 | Wang et al. |
| 7,033,594 B2 | 4/2006 | Low et al. |
| 7,128,893 B2 | 10/2006 | Leamon et al. |
| 7,223,380 B2 | 5/2007 | Yang et al. |
| 7,381,535 B2 | 6/2008 | Perez et al. |
| 7,601,332 B2 | 10/2009 | Vlahov |
| 7,740,854 B2 | 6/2010 | Low et al. |
| 7,977,058 B2 | 7/2011 | Low |
| 8,043,602 B2 | 10/2011 | Jallad et al. |
| 8,043,603 B2 | 10/2011 | Kennedy et al. |
| 8,383,354 B2* | 2/2013 | Low ............................. 435/7.1 |
| 8,388,977 B2 | 3/2013 | Low et al. |
| 2001/0031252 A1 | 10/2001 | Low et al. |
| 2002/0127181 A1 | 9/2002 | Edwards et al. |
| 2002/0192157 A1 | 12/2002 | Low et al. |
| 2003/0162234 A1 | 8/2003 | Jallad et al. |
| 2003/0198643 A1 | 10/2003 | Lu |
| 2003/0219375 A1 | 11/2003 | Piwnica-Worms |
| 2004/0033195 A1 | 2/2004 | Leamon et al. |
| 2004/0057900 A1 | 3/2004 | Edwards et al. |
| 2004/0136910 A1 | 7/2004 | Kennedy et al. |
| 2004/0184990 A1 | 9/2004 | Larsen et al. |
| 2004/0242582 A1 | 12/2004 | Green et al. |
| 2005/0002942 A1 | 1/2005 | Vlahov et al. |
| 2005/0026866 A1 | 2/2005 | Pawelek |
| 2005/0227985 A9 | 10/2005 | Green et al. |
| 2005/0244336 A1 | 11/2005 | Low |
| 2006/0002891 A1 | 1/2006 | Pouletty |
| 2006/0067946 A1 | 3/2006 | Low et al. |
| 2006/0134002 A1 | 6/2006 | Lin |
| 2006/0182687 A1 | 8/2006 | Yang et al. |
| 2006/0204565 A1 | 9/2006 | Low et al. |
| 2007/0009434 A1 | 1/2007 | Low et al. |
| 2007/0031334 A1 | 2/2007 | Leamon |
| 2007/0231266 A1 | 10/2007 | Low et al. |
| 2007/0276231 A1 | 11/2007 | Low et al. |
| 2008/0119475 A1 | 5/2008 | Low et al. |
| 2008/0138396 A1 | 6/2008 | Low et al. |
| 2008/0254499 A1 | 10/2008 | Low et al. |
| 2009/0012009 A1 | 1/2009 | Low et al. |
| 2010/0055735 A1 | 3/2010 | Low et al. |
| 2010/0322854 A1 | 12/2010 | Low et al. |
| 2011/0044897 A1 | 2/2011 | Low et al. |
| 2011/0189086 A1 | 8/2011 | Low |
| 2012/0003151 A1 | 1/2012 | Low et al. |
| 2012/0276191 A1 | 11/2012 | Low et al. |
| 2012/0301397 A1 | 11/2012 | Low et al. |

FOREIGN PATENT DOCUMENTS

| | | |
|---|---|---|
| WO | 01/39806 | 6/2001 |
| WO | 01/47552 | 7/2001 |
| WO | 01/74382 | 10/2001 |
| WO | 01/91807 | 12/2001 |
| WO | 02/087424 | 11/2002 |
| WO | 2004/044227 | 5/2004 |
| WO | 2004/069159 | 8/2004 |
| WO | 2004/110250 | 12/2004 |
| WO | 2005/049579 | 6/2005 |
| WO | 2005/067644 | 7/2005 |
| WO | 2005/087275 | 9/2005 |
| WO | 2006/012527 | 2/2006 |
| WO | 2006/034046 | 3/2006 |
| WO | 2006/065943 | 6/2006 |
| WO | 2006/071754 | 7/2006 |
| WO | 2006/101845 | 9/2006 |
| WO | 2007/001466 | 1/2007 |
| WO | 2007/006041 | 1/2007 |
| WO | 2007/038346 | 4/2007 |
| WO | 2008/057437 | 5/2008 |
| WO | 2008/098112 | 8/2008 |
| WO | 2008/148001 | 12/2008 |
| WO | 2009/002993 | 12/2008 |
| WO | 2009/026177 | 2/2009 |

OTHER PUBLICATIONS

Antohe et al., "Increased uptake of folate conjugates by activated macrophages in experimental hyperlipemia", Cell Tissue Research, vol. 320, No. 2, pp. 277-285, May 2005.

Aviram et al., "Intralipid infusion abolishes ability of human serum to cholesterol-load cultured macrophages", Arteriosclerosis, vol. 9, pp. 67-75, 1989.

Ballou et al., "Tumor labeling in vivo using cyanine-conjugated monoclonal antibodies", Cancer Immunol Immunother, vol. 41, pp. 257-263, 1995.

Barrera et al., "Synovial macrophage depletion with clodronate-containing liposomes in rheumatoid arthritis", Arthritis and Reheumatism, vol. 43, pp. 1951-1959, 2000.

Beaumont et al., "Selective Fluorodenitration of Chloronitroaromatics", J. Fluorine Chem., vol. 63, pp. 25-30, 1993.

Becker et al., "Macromolecular Contrast Agents for Optical Imaging of Tumors: Comparison of Indotricarbocyanine-labeled Human Serum Albumin and Transferrin", Photochemistry and Photobiology, vol. 72, No. 2, pp. 234-241, May 14, 2000.

U.S. Appl. No. 61/235,220, filed Aug. 19, 2009, Low et al.

U.S. Appl. No. 61/157,847, filed Mar. 5, 2009, Low et al.

Bettio et al, "Synthesis and Preclinical Evaluation of a Folic Acid Derivative Labeled with 18F for PET Imaging of Folate Receptor-Positive Tumors", The Journal of Nuclear Medicine, vol. 47, No. 7, pp. 1153-1160, 2006.

Boechat et al., Fluorodenitrations Using Tetramethylammonium Fluoride, J. Soc. Chem, Commun., pp. 921-992, 1993.

Boente et al., "Screening, imaging, and Early Diagnosis of Ovarian Cancer", Clinical Obstetrics and Gynecology, vol. 37, No. 2, pp. 377-391, Jun. 1994.

Budinger et al., "New Approaches to Targeting Arthritis with Radiopharmaceuticals", The Journal of Rheumatology, 22(1) Supp: 62-67, 1995.

Burke et al., "Book Review. The Macrophage", British Journal of Cancer, vol. 89, p. 421, 2003.

Campbell et al., "Folate-binding Protein is a Marker for Ovarian Cancer", Cancer Research, vol. 51, pp. 5329-5338, Oct. 1991.

Canis et al., "Lapascopic Diagnosis of Adnexal Cystic Masses: A 12-Year Experience With Long-Term Follow-Up", Obstetrics & Gynecology, vol. 83, No. 5, pp. 707-712, May 1994.

Case, "Ultrasound Physics and Instrumentation, Surgical Clinics of North America", vol. 78, No. 2, pp. 197-217, Apr. 1998.

Chen et al., "MicroPET Imaging of Brain Tumor Angiogenesis with 18F-Labeled PEGylated RGD Peptide", European Journal of Nuclear Medicine and Molecular Imaging, vol. 31, No. 8, pp. 1081-1089, Aug. 2004.

Ching-Hsuan Tung et al., "Preparation of a Cathepsin D Sensitive Near-Infrared Fluorescence Probe for Imaging", American Chemical Society, vol. 10, No. 5, pp. 692-696, 1999.

Cochlovius, "Therapeutic Antibodies", Modern Drug Discovery, pp. 33-38, 2003.

Cohen et al., "Screening for ovarian cancer: The role of noninvasive imaging techniques", Am J. Obstet Gynecol., vol. 170, No. 4, pp. 1088-1094, 1994.

Cohen et al., "Three-Dimensional Power Doppler Ultrasound Improves the Diagnostic Accuracy for Ovarian Cancer Prediction", Gynecologic Oncology, vol. 82, pp. 40-48, 2001.

Cox et al., "Anhydrous, Tetrabutylammonium Fluoride: A Mild but Highly Efficient Source of Nucleophilic Fluoride Ion", J. Org. Chem., No. 49, pp. 3216-3219, 1984.

Degrado et al., "Synthesis and Evaluation of (18)F-Labeled Choline Analogs as Oncologic PET Tracers", J. Nuclear Medicine, vol. 42, No. 12, pp. 1805-1814, 2001.

DePriest et al., "Transvaginal Sonography as a Screening Method for the Detection of Early Ovarian Cancer", Gynecologic Oncology, vol. 65, No. GO974705, pp. 408-414, 1997.

U.S. Appl. No. 12/526,096, filed Aug. 6, 2009, Low et al.

(56) References Cited

OTHER PUBLICATIONS

Feldman et al., "Anti-TNFa Therapy is Useful in Rheumatoid Arthritis and Crohn's Disease: Analysis of the Mechanism of Action Predicts Utility in Other Diseases", Transplant. Proc., 30, pp. 4126-4127, 1998.

Forstner et al., "CT and MRI of ovarian cancer", Abdominal Imaging, vol. 20, pp. 2-8, 1995.

Garg et al., "Fluorine-18 Labeling of Monoclonal Antibodies and Fragments with Preservation of Immunoreactivity", Bioconjugate Chem., vol. 2, No. 1, pp. 44-49, 1991.

Giroldo et al., "An Unusually Fast Nucleophilic Aromatic Displacement Reaction: The Gas-Phase Reaction of Fluoride Ions with Nitrobenzene", Angew. Chem. Int. Ed., No. 43, pp. 3588-3590, 2004.

Godwin et al., "The synthesis of biologically active pteroyloligo-g-L-glutamates (folic acid conjugates): Evaluation of (3H) pteroylheptaglutamate for metabolic studies", Journal of Biological Chemistry. vol. 247, pp. 2266-2271, Apr. 1974.

Gotoh, "Causes and treatment of rheumatoid arthritis; recent trend I. Progress in pathogenesis of rheumatoid arthritis; role of macrophages and dendritic cells", Pharma Nedica, Japan Medical Review Co., Ltd., Tokyo, 17(10): 35-39, 1999.

Greenman, Y., et al., "Heterogeneous Expression of Two Somatostatin Receptor Subtypes in Pituitary Tumors," Journal of Clinical Endocrinology and Metabolism, vol. 78, No. 2, pp. 398-403, 1994.

Hamacher et al., "No-Carrier-Added Nucleophilic 18F-Lavelling in an Electrochemical Cell Exemplified by the Routine Production of [18F]altanserin", Applied Radiation and Isotopes, No. 64, pp. 989-994, 2006.

Harris et al., "Human leukemic models of myelomonocytic development: a review of the HL-60 and U937 cell lines", Journal of Leukocyte Biology, vol. 37., No. 4, pp. 407-422, 1985.

Holmgren et al., "Strategies for the Induction of Immune Responses At Mucosal Surfaces Making Use of Cholera Toxin B Subunit As Immunogen, Carrier, and Adjuvant", Am. J. Trop Med Hyd, 50, pp. 42-54, 1994.

Hynes et al., "Quinazolines as Inhibitors of Dihydrofolate Reductase. 4. Classical Analogues of Folic and Isofolic Acids", Journal of Medicinal Chemistry, vol. 20, No. 4, pp. 588-591, 1977.

Jager et al., "Resection guided by antibodies (REGAJ): a diagnostic procedure during second-look operation in ovarian cancer patients", Depts of Obstetrics, Gynecology and Nuclear Medicine, Univ of Erlangen-Nurnberg, pp. 18-20, 1990.

Johnstrom et al., "18F-Endothelin-1, a Positron Emission Tomography (PET) Radioligand for the Endothelin Receptor System: Radiosynthesis and In Vivo Imaging Using MicroPET", Clinical Science, vol. 103, Suppl. 48, pp. 45-85, 2002.

Karlan, "The Status of Ultrasound and Color Doppler Imaging for the Early Detection of Ovarian Cancer", Cancer Investigation, vol. 15, No. 3, pp. 265-269, 1997.

Karlan et al., "Ovarian Cancer Screening: The Role of Ultrasound in Early Detection", Cancer Supplement, vol. 76, No. 10, pp. 2011-2015, Nov. 1995.

Karsten et al., "Towards Usage-Based Accounting: Applying Policy-Based Intelligent Agents, ITC 15". Elsevier Science B.V., pp. 633-642, 1997.

Kennedy et al., "Evaluation of Folate Conjugate Uptake and Transport by the Choroid Plexus of Mice", Pharmaceutical Research, vol. 20, No. 5, p. 714-719, May 2003.

Kennedy et al., "Optical imaging of metastatic tumors using a folate-targeted fluorescent probe", J. of Biomedical Optics, vol. 8, No. 4, pp. 636-641, Oct. 2003.

Kim et al., "Synthesis and Biological Activity of 10-Thia-10-deaza Analogs of Folic Acid, Pteroic Acid, and Related Compounds", Journal of Medicinal Chemistry, vol. 18, No. 8, pp. 776-780, 1975.

Kinne et al., "Macrophage in rheumatoid arthritis", Arthritis Research, vol. 2, No. 3, pp. 189-202, 2000.

Konda et al., "Development of a Tumor-Targeting MR Contrast Agent Using the High-Affinity Folate Receptor", Investigative Radiology, vol. 35, No. 1, pp. 50-57, 2000.

Kramer, "Basic Principles of Magnetic Resonance Imaging", Radiological Clinics of North America, vol. 22, No. 4, pp. 765-778, Dec. 1984.

Kuroiwa et al., "Development of a Fluorescein Operative Microscope for Use During Malignant Glioma Surgery", Elsevier Science Inc., vol. 50, pp. 41-49, 1998.

Leamon et al., "Folate-mediated targeting: from diagnosis to drug and gene therapy", DDT vol. 6 No. 1 44-51, Jan. 2001.

Leamon et al., "Synthesis and Biological Evaluation of EC140: A Novel Folate—Targeted Cinca Alkaloid Conjugate", Bioconjugate Chem., vol. 17, No. 5, pp. 1226-1232, 2006.

Leamon et al., "Synthesis and Biological Evaluation of EC20: A New Folate-Derived, 99mTc-Based Radiopharmaceutical", Bioconjugate Chemistry, vol. 13, No. 6, pp. 1200-1210, 2002.

Leamon et al., "Selective Targeting of Malignant Cells with Cytotoxin-Folate Conjugates", J. Drug Targeting 2: 101-112, 1994.

Lee et al., "Folic Acid Antagonists. Methotrexate Analogs Containing Spurious Amino Acids. Dichlorohomofolic Acid", Journal of Medicinal Chemistry, vol. 17, No. 3, pp. 326-330, 1974.

Lemaire et al., "Fluorine-18-Altanserin: A Radioligand for the Study of Serotonin Receptors with PET: Radiolabeling and In Vivo Biologic Behavior in Rats", The Journal of Nuclear Medicine. vol. 32, No. 12, pp. 2266-2272, Dec. 1991.

Licha et al., "Hydrophilic Cyanine Dyes as Contrast Agents for Near-infrared Tumor Imaging: Synthesis, Photophysical Properties and Spectroscopic in vivo Characterization", Photochemistry and Photobiology, vol. 72, No. 3, pp. 392-398, 2000.

Liotta et al., "The Chemistry of "Naked" Anions. I. Reactions of the 18-Crown-6 Complex of Potassium Fluoride with Organic Substrates in Aprotic Organic Solvents", Journal of American Chemical Society, vol. 96, No. 7, pp. 2250-2252, Apr. 3, 1974.

Liu-Wu et al., "Identification and Analysis of Macrophage-Derived Foam Cells from Human Atherosclerotic Lesions by Using a 'Mock' FL3 Channel in Flow Cytometry", Cytometry, vol. 29, No. 2, pp. 155-164, 1997.

Low et al., "Ovarian Cancer: Comparison of findings with Perfluorocarbon-enhanced MR Imaging, In-111-CYT-103 Immunoscintigraphy, and CT", Depts of Diagnostic Rad and Onc, Sharp Memorial Hospital, vol. 195, No. 2, pp. 391-400, 1995.

Lu et al., "Folate-Targeted Enzyme Prodrug Cancer Therapy Utilizing Penicillin-V Amidase and a Doxorubicin Prodrug", J. Drug Targeting 7:43-53, 1999.

Mahmood et al, "Near Infrared Optical Imaging for Protease Activity for Tumor Detection", Radiology, 213:866-870, 1999.

Maiman et al., "Laproscopic Excision of Ovarian Neoplasm Subsequently Found to Be Malignant", Obstetrics & Gynecology, vol. 77, No. 4, pp. 563-565, Apr. 1991.

Mancini et al., "Relative contributions of apolipoprotein A and apolipoprotein B to the development of fatty lesions in the proximal aorta of mice", Arterioscler. Thromb. Vasc. Biol., vol. 15, pp. 1911-1916, 1995.

Mantovani et al., "Folate Binding Protein Distribution in Normal Tissues and Biological Fluids From Ovarian Carcinoma Patients as Detected by the Monoclonal Antibodies Mov 18 and Mov 19", European Journal of Cancer, vol. 30A, No. 3, pp. 363-369, 1994.

Mathias et al., "Preparation of 66Ga- and 68GA-labeled GA(III)-deferoxamine-folate as potential folate-receptor-targeted PET radiopharmaceuticals", Nuclear Medicine and Biology, vol. 30, pp. 725-731, 2003.

Matsuyama et al., "Clinical significance of the folate receptor beta expression in rheumatoid synovial macrophages", Rheumatoid, Japan College of Rheumatology, 41(2): 265, 2001.

Matsuyama et al., "Activation and pathological significance of macrophages in rheumatoid synovitis", Clinical Immunity, Japan, Kagaku Hyoronsha, Tokyo, 30(2): 214-219, 1998.

Mestas et al. "Of Mice and Not Men: Differences between Mouse and Human Immunology", J. of Immunology, 172, pp. 2731-2738, 2004.

Mukasa et al., "Function analysis of folate receptor-β in a RA synovial membrane macrophage cell line", Rheumatoid, Japan College of Rheumatology, 40(2): 378, 2000.

Mulherin et al., "Synovial tissue macrophage populations and articular damage in rheumatoid arthritis", Arthritis and Rheumatism, vol. 39, No. 1, pp. 115-124, 1996.

(56) References Cited

OTHER PUBLICATIONS

Murakami et al., "18F-Labelled Annexin V: A PET Tracer for Apoptosis Imaging", European Journl of Nuclear Medicine and Molecular Imaging, vol. 31, No. 4, pp. 469-474, Apr. 2004.
U.S. Appl. No. 13/723,350, filed Dec. 21, 2012, Jallad et al.
Nagayoshi et al., "Effectiveness of Anti-Folate Receptor β Antibody Conjugated with Truncated *Pseudomonas* Exotoxin in the Targeting of Rheumoid Arthritis Synovial Macrophages", Arthritis and Rheumatism, vol. 52, pp. 2666-2675, Sep. 2005.
Nair et al., "Folate Analogues Altered in the C9-N10 Bridge Region. 10-Oxafolic Acid and 10-Oxaaminopterin", Journal of Medicinal Chemistry, vol. 19, No. 6, pp. 825-829, 1976.
Nair et al., "Folate Analogues Altered in the C9-N10 Bridge Region: 11-Thiohomofolic Acid", Journal of Medicinal Chemistry, vol. 22, No. 7, pp. 850-855, 1979.
Nair et al., "Folate Analogues Altered in the C9-N10 Bridge Region. 14. 11-Oxahomofolic Acid, a Potential Antitumor Agent", Journal of Medicinal Chemistry, vol. 23, pp. 59-65, 1980.
Nair et al., "Folate Analogues Altered in the C9-N10 Bridge Region. 18. Synthesis and Antitumor Evaluation of 11-Oxahomoaminopterin and Related Compounds", Journal of Medicinal Chemistry, vol. 24, pp. 1068-1073, 1981.
Nair et al., "Folate Analogues. 20. Synthesis and Antifolate Activity of 1, 2, 3, 4, 5, 6,—Hexahydrohomofolic Acid", Journal of Medicinal Chemistry, vol. 26, pp. 135-140, 1983.
Nair et al., "Folate Analogues. 21. Synthesis and Antifolate and Antitumor Activities of N10- (Cyanomethyl)-5,8-dideazafolic Acid", Journal of Medicianal Chemistry, vol. 26, pp. 605-607, 1983.
Nair et al., "Folate Analogues. 22. Synthesis and Biological Evaluation of Two Analogues of Dihydrofolic Acid Processing a 7,8-Dihydro-8-oxapterin Ring System", Journal of Medicinal Chemistry, vol. 26, 1164-1168, 1983.
U.S. Appl. No. 13/723,356, filed Dec. 21, 2012, Jallad et al.
Nakashima-Matsushita et al, "Selective expression of folate receptor beta and its possible role in methotrexate transport in synovial macrophages from patients with rheumatoid arthritis", Arthritis Rheum. 42(8): 1609-1616, 1999.
Nehzat et al. "Four ovarian cancers diagnosised during laproscopic management of 1011 women with adnexal masses", Am J Obstet Gynecol., vol. 167, No. 3, pp. 790-796, Sep. 1992.
Oatis et al., "Synthesis of Quinazoline Analogues of Folic Acid Modified at Position 10", Journal of Medicinal Chemistry, vol. 20, No. 11, pp. 1393-1396, 1977.
Olma et al., "4-[18F]fluorophenyl ureas via carbamate-4-nitrophenyl esters and 4-[18F]Fluoroaniline", Journal of Labeled Compd. And Radiopnarm, vol. 49, pp. 1037-1050, 2006.
Paigen et al., "Variation in susceptibility to atherosclerosis among inbred strains of mice", Atherosclerosis, vol. 57, No. 1, pp. 65-73, 1985.
Paulos et al. "Folate Receptor-Mediated Targeting of Therapeutic and Imaging Agents to Activated Macrophages in Rheumatoid Arthritis", Advanced Drug Delivery Reviews, vol. 56, No. 8, pp. 1205-1217, 2004.
Pelegrin et al., "Antibody-Fluorescein Conjugates for Photoimmunodiagnosis of Human Colon Carcinoma in Nude Mice", Institute of Biochemistry, University of Lausanne, vol. 67, No. 10, pp. 2529-2537, 1991.
Plante et al., "Polyglutamyl and Polylysyl Derivatives of the Lysine Analogues of Folic Acid and Homofolic Acid", Journal of Medicinal Chemistry, vol. 19, No. 11, pp. 1295-1299, 1976.
Rampone et al., "Ovarian cancer screening by transvaginal color Doppler ultrasonography", Minerva Ginecologica, vol. 53, Suppl. 1 al N 1, pp. 125-128, 2001.
Reddy et al., "Optimization of Folate-Conjugated Liposomal Vectors for Folate Receptor-Mediated Gene Therapy", J. Pharm. Sciences 88: 1112-1118, 1999.
Reddy et al., "Folate-Mediated Targeting of Therapeutic and Imaging Agents to Cancers", Critical Reviews in Ther. Drug Carrier Systems 15: 587-627, 1998.

Reddy et al., "Folate receptor specific anti-tumor activity of folate-mitomycin conjugates", Cancer Chemother. Pharmacol., 58(2): 229-36, 2006.
Reles et al., "Transvaginal Color Doppler Sonography and Conventional Sonography in the Preoperative Assessment of Adnexal Masses", Journal of Clinical Ultrasound, vol. 25, No. 5, pp. 217-225, Jun. 1997.
Roberts et al., "Folic Acid Analogs. Modifications in the Benzene-Ring Region. 2. Thiazole Analogs", Journal of Medicinal Chemistry, 15 (12): 1310-1312, 1972.
Roberts et al., "Folic Acid Analogs. Modifications in the Benzene-Ring Region. 1. 2'- and 3'- Azafolic Acids", Journal of Medicinal Chemistry, 14(2): 125-130, 1971.
Roberts et al., "Folic Acid Analogs. Modifications in the Benzene-Ring Region. 4. 3'- Ethyl - and 3'- Isopropylfolic Acids", Journal of Medicinal Chemistry, vol. 17, No. 2, pp. 219-222, 1974.
Rouzi et al., "Lapascopic Ovarian Cystectomy: Selection of Patients and Consequences of Rupture of Ovarian Malignancy", Annals of Saudi Medicine, vol. 17, No. 3, pp. 321-325, 1997.
Rudd et al., "Imaging Atherosclerotic Plaque Inflammation with [<18>F]-Fluorodeoxyglucose Positron Emission Tomography", Circulation, vol. 105, No. 23, pp. 2709-2710, 2002.
Sato et al., "Usefulness of Mass Screening for Ovarian Carcinoma Using Transvaginal Ultasonography", American Cancer Society, vol. 89, No. 3, pp. 582-588, Aug. 2000.
Sevick-Muraca et al., "Fluorescence and Absorption Contrast Mechanisms for Biomedical Optical Imaging Using Frequency-Domain Techniques", Photochemistry and Photobiology, vol. 66, No. 1, pp. 55-64, 1997.
Sheski et al., "Endoscopic Treatment of Early-Stage Lung Cancer", Division of Pulmonary, Allergy, Care, and Occupational Medicine at IU School of Medicine, vol. 7, No. 1, pp. 35-44, Jan./Feb. 2000.
Shoup et al., "Synthesis of Fluorine-18-Labeled Biotin Derivatives: Biodistribution and Infection Localization", J. Nuclear Medicine, vol. 35, No. 10, pp. 1685-1690, 1994.
Sijtsema et al., "Confocal Direct Imaging Raman Microscope: Design and Application in Biology", Applied Spectroscopy, vol. 52, Issue 3, pp. 348-355, 1998.
Sima et al., "Experimental obstructive coronary atherosclerosis in the hyperlipidemic hamster", J Submicrosc Cytol Pathol, vol. 22, No. 1, pp. 1-16, 1990.
Smart et al., "Protein kinase C activators inhibit receptor-mediated potocytosis by preventing internalization of caveolae", Journal of Cell Biology, vol. 124, No. 3, pp. 307-313, 1994.
Solomin et al., "Computerized Tomography in Ovarian Cancer", Gynecologic Oncology, vol. 15 pp. 48-55, 1983.
Sudimak et al., "Targeted drug delivery via the folate receptor", Advanced Drug Delivery Reviews, vol. 41, pp. 147-162, 2000.
Sun et al., "Anhydrous Tetrabutylammonium Fluoride", J. Am. Chem. Soc., vol. 127, No. 7, pp. 2050-2051, 2005.
Sun et al., "Room-Temperature Nucleophilic Aromatic Fluorination: Experimental and Theoretical Studies", Angew. Chem. Int. Ed., No. 45, pp. 2720-2725, 2006.
Sundstrum et al., "Establishment and characterization of a human histiocytic lymphoma cell line (U-937)", International Journal of Cancer, vol. 17, No. 5, pp. 565-577, 1976.
Sutcliffe-Goulden, "Solid Phase Synthesis of [18F]Labelled Peptides for Positron Emission Tomography", Bio. & Medicin. Chem. Letters, No. 10, pp. 1501-1503, 2000.
Tan et al., "A Complete Remote-Control System for Reliable Preparation of [18F]altanserin", Applied Radiation and Isotopes, vol. 50, pp. 923-927, 1999.
Temple, Jr. et al., "Synthesis of Pseudo Cofactor Analogues as Potential Inhibitors of the Folate Enzymes", Journal of Medicinal Chemistry, vol. 25, pp. 161-166, 1982.
Toffoli et al., "Expression of Folate Binding Protein as a Prognostic Factor for Response to Platinum-Containing Chemotherapy and Survival in Human Ovarian Cancer", Int. J. Cancer, vol. 79, pp. 121-126, 1998.
Toffoli et al., "Overexpression of Folate Binding Protein in Ovarian Cancers", Int. J. Cancer (Pred. Oncol.), vol. 74., pp. 193-198, 1997.

(56) References Cited

OTHER PUBLICATIONS

Turk et al., "Folate-targeted imaging of activated macrophage in rats with adjuvant-induced arthritis", Arthritis and Rheumatism, vol. 46, No. 7, pp. 1947-1955, 2002.
Urban, "Screening for ovarian cancer: We now need a definitive randomized trial", BMJ, vol. 319, pp. 1317-1318, Nov. 1999.
Van Noort et al., "Cell Biology of Autoimmune Diseases", International Review of Cytology, vol. 178, pp. 127-204, 1998.
Vo-Dinh et al., "In Vivo Cancer Diagnosis of the Esophagus Using Differential Normalized Fluorescence (DNF) Indices", Lasers in Surgery and Medicine, vol. 16, pp. 41-47, 1995.
Wang et al., "Chemokines and their role in cardiovascular diseases", TCM, vol. 8, pp. 169-174, 1998.
Weinstock et al., "Folic Acid Analogs. II. p-{[2,6-Diamino-8-purinyl)methyl]amino}—benzoyl-L-glutamic Acid and Related Compounds", Journal of Medicinal Chemistry, 1970, 13(5): 995-997, 1970.
Weissleder et al., "In vivo imaging of tumors with protease-activated near-infrared fluorescent probes", Nature Biotechnology, vol. 17, pp. 375-378, Apr. 1999.
Weitman et al., "The folate receptor in central nervous system malignancuies of childhood", Journal of Neuro-Oncology, vol. 21, pp. 107-112, 1994.
Whitehurst et al., "Development of an alternative light source to lasers for biomedical applications", SPIE, vol. 2629, pp. 291-298, 1993.
Wu et al., "Expression of Folate Receptor Type a in Relation to Cell Type Malignancy, and Differentiation in Ovary, Uterus and Cervix", Cancer Epidemiology, Biomarkers & Prevention, vol. 8, pp. 775-782, 1999.
Yavorsky et al., "Antiparticles", Handbook on Physics, pp. 339-340, 1984.
Zeisel et al., "Choline, an Essential Nutrient for Humans", The Faseb Journal, vol. 5, No. 7, pp. 2093-2098, 1991.
Delaloye et al., "Tumor imaging with monoclonal antibodies", Seminars in Nuclear Medicine, 25:144-164, 1995.
Reubi, "The role of peptides and their receptors as tumor markers", Endocrinology & Metabolism Clinics of North America, 22: 917-939, 1993.
Garin-Chesa et al., "Trophoblast and ovarian cancer antigen LK26. Sensitivity and specificity in immunopathology and molecular identification as a folate-binding protein", American Journal of Pathology, 142: 557-567, 1993.
Patrick et al., "Folate receptors as potential therapeutic targets in choroid plexus tumors of SV40 transgenic mice", Journal of Neuro-Oncology, 32: 111-123, 1997.
Weitman et al., "Distribution of the folate receptor GP38 in normal and malignant cell lines and tissues", Cancer Research, 52: 3396-3401, 1992.
Mathias et al., "Indium-111-DTPA-folate as a potential folate-receptor-targeted radiopharmaceutical", Journal of Nuclear Medicine, 39: 1579-1585, 1998.
Acosta et al., "Chromoendoscopy—where is it useful?", Journal of Clinical Gastroenterology, 27:13-20,1998.
Fleischer, "Chromoendoscopy and magnification endoscopy in the colon", Gastrointestinal Endoscopy, 49: S45-49, 1999.
Stepp et al., "Fluorescence endoscopy of gastrointestinal diseases: basic principles, techniques, and clinical experience", Endoscopy, 30: 379-386, 1998.
Ballou et al., "Tumor detection and visualization using cyanine fluorochrome-labeled antibodies", Biotechnology Progress, 13: 649-658, 1997.
Licha et al., "Synthesis, characterization, and biological properties of cyanine-labeled somatostatin analogues as receptor-targeted fluorescent probes", Bioconjugate Chemistry, 12: 44-50, 2001.
Becker et al., "Receptor-targeted optical imaging of tumors with near-infrared fluorescent ligands", Nature Biotechnology, 19: 327-331, 2001.

Terpetschnig et al., "Synthesis of squaraine-N-hydroxysuccinimide esters and their biological application as long-wavelength fluorescent labels", Analytical Biochemistry, 217: 197-204, 1994.
Mujumdar et al., "Cyanine dye labeling reagents containing isothiocyanate groups", Cytometry, 10: 11-19, 1989.
Wang et al., "Design and synthesis of [111In]DTPA-folate for use as a tumor-targeted radiopharmaceutical", Bioconjugate Chemistry, 8: 673-679, 1997.
Dimartino et al., "Antiarthritic and immunoregulatory activity of spirogermanium", Journal of Pharmacology an Experimental Therapeutics, 236: 103-110, 1986.
Ross et al., "Differential regulation of folate receptor isoforms in normal and malignant tissues in vivo and in established cell lines. Physiologic and clinical implications", Cancer, 73: 2432-2443, 1994.
Ross et al., "Folate receptor type beta is a neutrophilic lineage marker and is differentially expressed in myeloid leukemia", Cancer, 85: 348-357, 1999.
Curtin et al., "Stage IV ovarian cancer: impact of surgical debulking", Gynecologic Oncology, 64: 9-12, 1997.
Munkarah et al., "Prognostic significance of residual disease in patients with stage IV epithelial ovarian cancer", Gynecologic Oncology, 64: 13-17, 1997.
Murolo et al., "Ultrasound examination in ovarian cancer patients. A comparison with second look laparotomy", Journal of Ultrasound in Medicine, 8: 441-443, 1989.
Piver et al., "Second-look laparoscopy prior to proposed second-look parotomy", Obstetrics and Gynecology, 55: 571, 1980.
Bell et al., "Intraoperative radioimmunodetection of ovarian cancer using monoclonal antibody B72.3 and a portable gamma-detecting probe", Obstetrics and Gynecology, 76: 607-677, 1990.
Reuter et al., "Detection of colorectal carcinomas by intraoperative RIS in addition to preoperative RIS: surgical and immunohistochemical findings", European Journal of Nuclear Medicine, 19: 102-109, 1992.
Hornung et al., "Minimally-invasive debulking of ovarian cancer in the rat pelvis by means of photodynamic therapy using the pegylated photosensitizer PEG-m-THPC", British Journal of Cancer, 81: 631-637, 1999.
Folli et al., "Antibody-indocyanin conjugates for immunophotodetection of human squamous cell carcinoma in nude mice", Cancer Research, 54: 2643-2649, 1994.
Bannwarth et al., "Methotrexate in rheumatoid arthritis. An update", Drugs, 47: 25-50, 1994.
Bettegowda, et al., Proc. Natl. Acad. ScL U.S.A., 102: 1145-1150, 2005.
Bunce, et al., Infect. Immun., 60: 2636-2640, 1992.
Claassen E. et al., "Preparation and characteristics of dichloromethylene diphosphonate-containing liposomes," J. Microencapsul., 3: 109-14, 1986.
Marceau et al., Bioorganics and Medical Chemistry Letters, 15(24): 5442-5445, 2005.
Novabiochem® Letters, "Resins for the synthesis of biotinylated and fluorescently-labeled peptides," Jan. 2004, pp. 1-4, 2004.
Novabiochem® Letters, "Products for peptide ligation," Feb. 2004, pp. 1-4, 2004.
Novabiochem® Letters, "Amino acids for Fmoc SPPS," Mar. 2004, pp. 1-4, 2004.
Novabiochem® Letters, "PEG reagents," Apr. 2004, pp. 1-4, 2004.
Leamon et al., "Folate-Liposome-Mediated Antisense Oligodeoxynucleotide Targeting to Cancer Cells: Evaluation in Vitro and in Vivo", Bioconjugate Chem., 14, 738-747, 2003.
Leamon et al., "Folate-mediated Drug Delivery: Effect of Alternative conjugate Chemistry", Journal of Drug Targeting, col. 7, No. 3, 157-169, 1999.
Marecos et al., "Antibody-Mediated versus Nontargeted Delivery in a Human Small Cell Lung Carcinoma Model", Bioconjugate Chemistry, 9:184-191 (1998).
"Osteomyelitis", XP-002569963, URL:http://emedicine.medscape.com/article/785020-overview>, retrieved Feb. 22, 2010.
Kennedy MD, "Folate-targeted imaging agents," Thesis submitted to the faculty of Purdue University in partial fulfillment of the requirements for the degree of Doctor of Philosophy, published Nov. 2004.

(56) References Cited

OTHER PUBLICATIONS

Holladay et al., "Riboflavin-mediated delivery of a macromolecule into cultured human cells," *Biochim Biophys Acta* 1426(1): 195-204 (1999).

Kennedy et al., "Optical imaging of metastatic tumors using a folate-targeted fluorescent probe," *J. of Biomedical Optics*, vol. 8, No. 4, pp. 636-641, Oct. 2003.

Low, P.S., Leamon, C.P., Reddy, J.A., Green, M.A., Mathias, C., Turk, M.J., Waters, D.J., Lu, J., Lee, R.J. and Kennedy, M., "Folate-Mediated Delivery of Therapeutic and Imaging Agents to Cancer Tissues In Vivo," International Symposium on Tumor Targeted Delivery Systems, Bethesda, Maryland. British Journal of Pharmacology, vol. 134 (Abstract), 2001.

Phelps et al., Journal of Nuclear Medicine, 1975, 16(3): 210-224.

Snook et al., Br. J. Cancer, 1990, 62 (Suppl. X): 89-91.

Patton, Radiographics, 1998, 18: 995-1007.

Barnes, H. H., et al., "Purification of Catechol Siderophores by Boronate Affinity Chromatography: Identification of Chrysobactin From *Erwinia carotovora subsp. carotovora*", 1999, *BioMetals*, vol. 12, pp. 83-87.

Collins, Peter, et al., "Monosaccharides, Their Chemistry and Their Roles in Natural Products", 1995 *Wiley Publishers*, Book Reference.

Georgakoudi, Irene, et al., "In Vivo Flow Cytometry: A New Method for Enumerating Circulating Cancer Cells", Aug. 1, 2004, *Cancer Research*, No. 64, pp. 5044-5047.

Hanessian, Stephen, "Preparative Carbohydrate Chemistry", 1997 *Marcel Dekker, Inc.*, Book Reference.

Idanpaan-Heikkila, Ilona, et al., "Oligosaccharides Interfere With the Establishment and Progression of Experimental Pneumococcal Pneumonia", 1997, *The Journal of Infectious Diseases*, No. 176, pp. 704-712.

Iijima, Masatomi, et al., "IC202A, A New Siderophore With Immunosuppressive Activity Produced by *Streptoalloteichus* sp. 1454-19. I. Taxonomy, fermentation, isolation and biological activity.", Jan. 1999, *The Journal of Antibiotics* (Toyko), vol. 52, No. 1, pp. 20-24.

Lingwood, Clifford A., "Oligosaccharide Receptors for Bacteria: A View to a Kill", 1998, *Curr Opin Chem Biol.*, pp. 695-700.

Michelson, Alan D., et al., "Evaluation of Platelet Function by Flow Cytometry", 2000, *Methods*, vol. 21, pp. 259-270.

Novak, J., et al., "In Vivo Flow Cytometer for Real-Time Detection and Quantification of Circulating Cells", Jan. 1, 2004 *Optics Letters*, vol. 29, No. 1, pp. 77-79.

Ratledge, Colin, et al., "The Occurrence of Carboxymycobactin, The Siderophore of Pathogenic Mycobacteria, As a Second Extracellular Siderophore in *Mycobacterium smegmatis*", 1996 *Microbiology*, vol. 142, pp. 2207-2212.

Scharfman, Andree, et al., "*Pseudomonas aeruginosa* Binds to Neoglycoconjugates Bearing Mucin Carbohydrate Determinants and Predominantly to sialyl-Lewis x Conjugates", 1999, *Glycobiology*, vol. 9, No. 8, pp. 757-764.

Schalk, Isabelle J., et al., "Iron-Free Pyoverdin Binds to Its Outer Membrane Receptor FpvA in *Pseudomonas aeruginosa*: A New Mechanism for Membrane Iron Transport", 2001, *Molecular Microbiology*, vol. 39, No. 2, pp. 351-360.

Albrecht-Gary et al., "Bacterial Iron Transport: Coordination Properties of Pyoverdin PaA, a Peptidic Siderophore of *Pseudomonas aeruginosa*", 1994. *Inorg. Chem.*, 33 (26), pp. 6391-6402.

Henne, Walter A., et al., "Synthesis and Activity of a Folate Peptide Camptothecin Prodrug", (Aug. 9, 2006), *Bioorganic & Medicinal Chemistry Letters*, vol. 16, pp. 5350-5355.

Tang, Hailun, et al., "Prostate Targeting Ligands Based on N-Acetylated α-Linked Acidic Dipeptidase", (2003), *Biochemical and Biophysical Research Communications*, vol. 307, pp. 8-14.

Wosikowski, Katja, et al., "In Vitro and in Vivo Antitumor Activity of Methotrexate Conjugated to Human Serum Albumin in Human Cancer Cells", (May 2003), *Clinical Cancer Research*, vol. 9, pp. 1917-1926.

Wiener et al., "Targeting Dendrimer-Chelates to Tumors and Tumor Cells Expressing the High-Affinity Folate Receptor," *Investigative Radiology*, 1997; 32(12):748-754.

Paulos et al., "Ligand Binding and Kinetics of Folate Receptor Recycling in Vivo: Impact on Receptor-Mediated Drug Delivery," Molecular Pharmacology, 2004; 66:1406-1414.

Chen et al., "In vivo imaging of proteolytic activity in atherosclerosis," Circulation, 2002, 105: 2766-2771.

NCBI, MeSH definition for Indocarbocyanine Green, 2 pages, Aug. 31, 2008.

Kanagaki et al., "Pituitary Gland and Parasellar Region," in *Magnetic Resonance Tomography*, Reiser et al. (eds.), 2008, p. 422.

He et al., "In vivo quantitation of rare circulating tumor cells by multiphoton intravital flow cytometry," Proc Nat Acad Sci USA, 2007; 104: 11760-11765.

Mathias et al., "Synthesis of [99mTc]DTPA-Folate and Its Evaluation as a Folate-Receptor-Targeted Radiopharmaceutical", Bioconj. Chem., 2000; 11:253-257.

Linder et al., "In Vitro & In Vivo Studies with α-and γ-Isomers of 99mTc-OXA-Folate Show Uptake of Both Isomers in Folate-Receptor (+) KB Cell Lines", Soc. Nucl. Med. Proc., May 2000; 41:5:119.

Ilgan et al., "99mTc-Ethylenedicysteine-Folate: A New Tumor Imaging Agent. Synthesis, labeling and Evaluation in Animals", Can. Biother. & Radiophar., 1998; 13:6:427-435.

Massoud et al., "Molecular imaging in living subjects: seeing fundamental biological processes in a new light", 2003, Genes Dev. 17: 545-580.

Caliceti et al., "Pharmacokinetic and biodistibution properties of poly9ethylene glycol)—protein conjugates", 2003, Adv. Drug Del. Rev. 55: 1261-1277.

Tamaki et al., "PET in Oncology" Jpn J Cancer Clin, 2003, 49(6): 531-535.

Remington: The Science & Practice of Pharmacy, 21th Edition (Lippincott Williams & Wilkins, 2005) (Book Reference).

Bendele et al., "Animal Models of Arthritis: Relevance to Human Disease", Toxicology Pathology, vol. 27, No. 1, pp. 134-142, 1999.

Kern, et al., "Evaluation of the Culprit Plaque and the Physiological Significance of Coronary Atherosclerotic Narrowings," Circulation, 2001; 103:3142-3149.

Pasterkamp et al. "Techniques characterizing the coronary atherosclerotic plaque: Influence on clinical decision making?", J. Amer. Coll. Cardiol. 36:13-21, 2000.

NCBI, MeSH definition for Indocarbocyanine Green, 2 pages. Aug. 31, 2008.

"Macrophages" from Wikipedia, updated Nov. 18, 2007.

Bock et al., "Sulfonamide Structure-Activity Relationships in a Cell-Free System. 2. Proof for the Formation of a Sulfonamide-Containing Folate Analog", Journal of Medicinal Chemistry, vol. 17, No. 1, pp. 23-28, 1974.

Bonasera et al., "The Synthesis of [26, 27-11C]Dihydroxyvitamin D3, a Tracer for Positron Emission Tomography (PET), Bioorganic & Medicinal Chemistry", Elsevier Science Ltd., vol. 9, pp. 3123-3128, 2002.

Nair et al., "Folate Analogues Altered in the C9-N10 Bridge Region: N10-Tosylisohomofolic Acid and N10-Tosylisohomoaminopterin", Journal of Medicinal Chemistry, vol. 21, No. 7, pp. 673-677, 1978.

Roberts, et al., "Folic Acid Analogs. Modifications in the Benzene-Ring Region. 3. Neohomofolic and Neobishomofolic Acids. An Improved Synthesis of Folic Acid and Its Analogs". Journal of Medicinal Chemistry, 16(6): 697-699, 1973.

Simionescu et al., "Prelesional modifications of the vessel wall in hyperlipidemic atherogenesis: Extracellular accumulation of modified and reassembled lipoproteins", Ann. NY Acad. Sci., vol. 598, pp. 1-16, 1990.

Wang et al. "Synthesis, Purification, and Tumor Cell Uptake of Ga-Deferoxamine-Folate, a Potential Radiopharmaceutical for Tumor Imaging", American Chemical Society, Bioconjugate Chem., 1996, 7(1): 56-62, 1996.

(56) References Cited

OTHER PUBLICATIONS

Westerhof et al., Carrier-and Receptor-Mediated Transport of Folate Antagonists Targeting Folate-Dependent Enzymes: Correlates of Molecular-Structure and Biological Activity, Molecular Pharmacology, 1995, 48: 459-471, 1995.

Folli et al., "Immunophotodiagnosis of colon carcinomas in patients injected with fluoresceinated chimeric antibodies against carcinoembryonic antigen", Proceedings of the National Academy of Sciences of the United States of America, 89: 7973-7977, 1992.

Low PS, Leamon CP, Reddy JA, Green MA, Mathias C, Turk MJ, Waters DJ, Lu J, Lee RJ, Kennedy MD, "Folate-mediated delivery of therapeutic and imaging agents to cancer tissue," Gene, Drug Therapy, and Molecular Biology (Abstract), 2000.

Tanaka, et al., "Digestive tract lesions and immunity," The Japanese Journal of Gastroenterology, 1994, vol. 91(2): 131-135.

Folate-FITC (http://www.medkoo.com/Anticancer-trials/EC-17.htm (downloaded on Aug. 8, 2013)).

Atherosclerosis (http://web.archive.org/web/20081207060136/http://en.wikipedia.org/wiki/Atherosclerosis (archived on Dec. 7, 2008)).

* cited by examiner

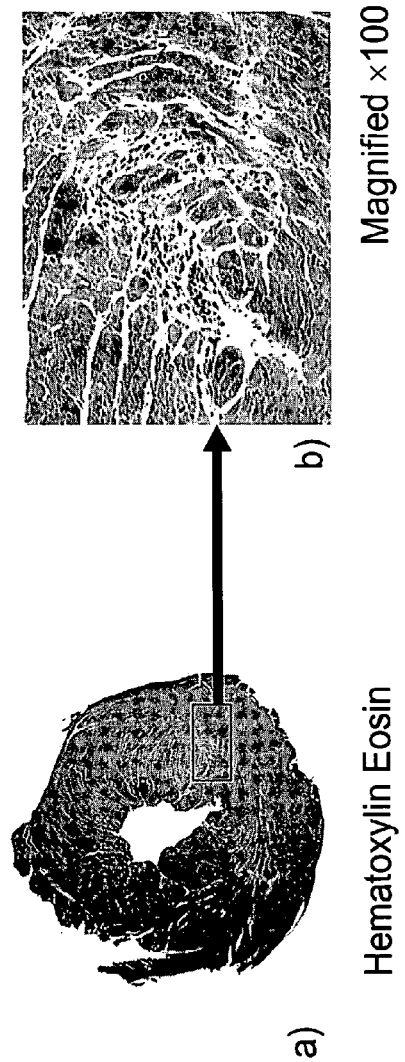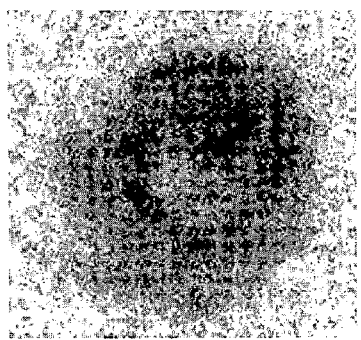
Fig. 12
Autoradiography mouse B
a) Hematoxylin Eosin
b) Magnified ×100
c) Tc-folate Hot / Cold =2.5

DIAGNOSTIC METHOD FOR ATHEROSCLEROSIS

CROSS REFERENCE TO RELATED APPLICATIONS

This application is a continuation application of U.S. application Ser. No. 13/083,121, filed Apr. 8, 2011, and issued as U.S. Pat. No. 8,383,354, which is a divisional application of U.S. application Ser. No. 11/022,088, filed Dec. 23, 2004, and issued as U.S. Pat. No. 7,977,058, which is a continuation-in-part application of PCT/US2004/016667, filed on May 27, 2004, which claims priority under 35 U.S.C. §119(e) to U.S. Provisional Application Ser. No. 60/474,731, filed on May 30, 2003, each of which is incorporated herein by reference.

FIELD OF THE INVENTION

This invention relates to a method for identifying/monitoring active atherosclerotic plaques. More particularly, ligands that bind to activated macrophages are conjugated to a chromophore or to a chemical moiety capable of emitting radiation for administration to a diseased host for identifying/monitoring active atherosclerotic plaques.

BACKGROUND AND SUMMARY OF THE INVENTION

Activated macrophages can participate in the immune response by nonspecifically engulfing and killing foreign pathogens within the macrophage, by displaying degraded peptides from foreign proteins on the macrophage cell surface where they can be recognized by other immune cells, and by secreting cytokines and other factors that modulate the function of T and B lymphocytes, resulting in further stimulation of immune responses. Activated macrophages can also contribute to the pathophysiology of disease in some instances. For example, activated macrophages can contribute to atherosclerosis, rheumatoid arthritis, autoimmune disease states, and graft versus host disease.

Atherosclerosis is initiated when a fatty streak forms within a blood vessel wall. Formation of fatty streaks is believed to result from accumulation of lipoprotein particles in the intima layer of the blood vessel wall, the layer of the vessel wall underlying the luminal endothelial cell layer. Lipoprotein particles can associate with extracellular matrix components in the intima layer and can become inaccessible to plasma antioxidants, resulting in oxidative modification of the lipoprotein particles. Such oxidative modification may trigger a local inflammatory response resulting in adhesion of activated macrophages and T lymphocytes to the luminal endothelium followed by migration into the intima layer. The oxidized lipoprotein particles themselves can act as chemoattractants for cells of the immune system, such as macrophages and T cells, or can induce cells in the vascular wall to produce chemoattractants. The atherosclerotic lesion then forms a fibrous cap with a lipid-rich core filled with activated macrophages. Atherosclerotic lesions that are unstable are characterized by local inflammation, and lesions that have ruptured and have caused fatal myocardial infarction are characterized by an infiltration of activated macrophages and T lymphocytes.

The present invention relates to a method of identifying/monitoring active atherosclerotic plaques in blood vessel walls. In accordance with the invention a ligand, that binds to a receptor which is preferentially expressed/presented on the surface of activated macrophages relative to resting macrophages, is conjugated to a chromophore or a chemical moiety capable of emitting radiation and the ligand conjugates are administered to a patient being evaluated for atherosclerosis. The ligand conjugates bind to activated macrophages associated with active atherosclerotic plaques and emit light (i.e., ligand-chromophore conjugates) or radiation (i.e., ligand-chemical moiety conjugates) and can be detected using a catheter-based device or by external imaging, such as by using X-ray detection. Accordingly, the ligand conjugates can be used to distinguish active atherosclerotic plaques containing activated macrophages from inactive plaques.

Methods are not presently available for distinguishing active and inactive atherosclerotic plaques. Because many unstable (i.e., active) atherosclerotic plaques, capable of rupturing and causing acute atherosclerotic syndromes do not produce luminal narrowing of blood vessels, particularly in the coronary circulation, the method of the present invention represents a significant advance in diagnosing the risk of myocardial infarction, and in evaluating the need for clinical intervention, in patients suffering from atherosclerosis.

In one embodiment, a method is provided of identifying/monitoring active atherosclerotic plaques associated with blood vessel walls wherein the plaques comprise activated macrophages having accessible binding sites for a ligand. The method comprises the steps of administering to a patient being evaluated for atherosclerosis an effective amount of a composition comprising a conjugate of the general formula

L-X wherein the group L comprises the ligand and the group X comprises a chromophore capable of emitting light under predetermined conditions, allowing sufficient time for the ligand conjugate to bind to activated macrophages associated with the active plaques, subjecting the blood vessel walls to the predetermined conditions using a catheter-based device, and identifying active plaques by detecting light emitted by the chromophore using a catheter-based device.

In another embodiment, a method is provided of identifying/monitoring active atherosclerotic plaques associated with blood vessel walls where the plaques comprise activated macrophages having accessible binding sites for a ligand. The method comprises the steps of administering to a patient suffering from atherosclerosis an effective amount of a composition comprising a conjugate of the general formula

L-X wherein the group L comprises the ligand and the group X comprises a chemical moiety capable of emitting radiation, allowing sufficient time for the ligand conjugate to bind to the activated macrophages associated with the active plaques, and identifying active plaques by detecting radiation emitted by the chemical moiety using a catheter-based device or by external imaging, such as by X-ray detection.

In these embodiments, the ligand can be any ligand that binds to a receptor which is preferentially expressed/presented on the surface of activated macrophages relative to resting macrophages. Such ligands include vitamins selected from the group consisting of folate, biotin, vitamin $B_{12}$, riboflavin, thiamine, and other vitamin receptor binding ligands.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12 shows A) an H & E stain of an atherosclerotic artery, B) an H & E stain, magnified 100×, of an atherosclerotic artery, and C) an autoradiograph of an atherosclerotic artery from a mouse injected with EC20.

DETAILED DESCRIPTION OF THE INVENTION

Figure 1:
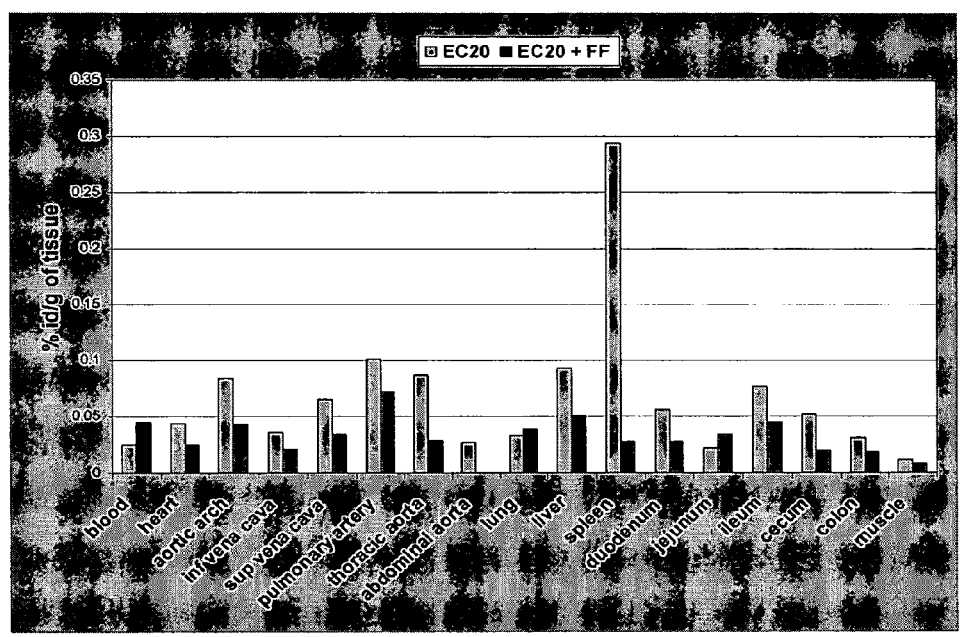
FIG. 1 shows the uptake of a folate-targeted $^{99m}$Tc chelating chemical moiety (EC20) in the organs of atherosclerotic Watanabe rabbits.

The present invention relates to a method of identifying/monitoring active atherosclerotic plaques in blood vessel walls. In accordance with the invention a ligand that binds to a receptor which is preferentially expressed/presented on the surface of activated macrophages relative to resting macrophages, is conjugated to a chromophore capable of emitting light or a chemical moiety capable of emitting radiation and the ligand conjugates are administered to a patient being evaluated for atherosclerosis. The ligand conjugates bind to activated macrophages associated with active atherosclerotic plaques. The light or radiation emitted by the ligand-chromophore conjugate or the chemical moiety, respectively, is detected using a catheter-based device or externally using such methods as X-ray detection. Accordingly, the ligand conjugates can be used to distinguish active atherosclerotic plaques, containing activated macrophages, from inactive plaques wherein the plaques are present in the arteries or veins of a patient being evaluated for atherosclerosis.

In accordance with the invention, the word "catheter" means any catheter, guidewire, or other device capable of transluminal delivery (i.e., delivery into the lumen of blood vessels) of optical energy or of radiation, and/or any catheter, guidewire, or other device capable of detecting, in the lumen of blood vessels, light or radioactivity emitted from the ligand conjugates used in accordance with the method of the present invention, and/or any catheter, guidewire, or other device capable of delivering a therapeutic drug to the lumen of blood vessels.

In accordance with the present invention, the ligand conjugates can be formed from a wide variety of ligands, including any ligand that binds to a receptor expressed or presented on the surface of activated macrophages that is not expressed/presented or is not present in significant amounts on the surface of resting macrophages. Such ligands include N-formyl peptides (e.g., f-Met-Leu-Phe), high mobility group factor 1 protein (HMGB1), hyaluronan fragments, HSP-70, toll-like receptor ligands, scavenger receptor ligands, co-receptors for antigen presentation, ligands that bind to the CD68, BER-MAC3, RFD7, CD4, CD14, and HLA-D markers on activated macrophages, ligands that bind to urokinase plasminogen activator receptors (e.g., the WX-360 peptide), antibodies, or fragments thereof, that bind preferentially to activated macrophages, and vitamins or receptor-binding vitamin analogs/derivatives. The ligand conjugates are capable of preferentially binding to activated macrophages compared to resting macrophages due to preferential expression of the receptor for the ligand on activated macrophages.

Acceptable vitamin moieties that can be used as ligands in accordance with the invention include niacin, pantothenic acid, folic acid, riboflavin, thiamine, biotin, vitamin $B_{12}$, and the lipid soluble vitamins A, D, E and K. These vitamins, and their receptor-binding analogs and derivatives, constitute the targeting entity that can be coupled with a chromophore or a chemical moiety, capable of emitting radiation, to form the ligand conjugates for use in accordance with the invention. Preferred vitamin moieties include folic acid, biotin, riboflavin, thiamine, vitamin $B_{12}$, and receptor-binding analogs and derivatives of these vitamin molecules, and other related vitamin receptor-binding molecules (see U.S. Pat. No. 5,688,488, incorporated herein by reference). Exemplary of a vitamin analog is a folate analog containing a glutamic acid residue in the D configuration (folic acid normally contains one glutamic acid in the L configuration linked to pteroic acid).

In the ligand conjugates of the general formula L-X in accordance with the present invention, the group L is a ligand capable of binding to activated macrophages as compared to resting macrophages as described above. In one embodiment the activated macrophage binding ligand is folic acid, a folic acid analog/derivative or other folate receptor binding molecules. In another embodiment the activated macrophage binding ligand is a specific monoclonal or polyclonal antibody or Fab or scFv (i.e., a single chain variable region) fragments of an antibody capable of preferential binding to activated macrophages as compared to resting macrophages.

Activated macrophages express a 38 kD GPI-anchored folate receptor that binds folate and folate-derivatized compounds with subnanomolar affinity (i.e., <1 nM). Importantly, covalent conjugation of small molecules, proteins, and even liposomes to folic acid does not alter the vitamin's ability to bind the folate receptor. Because most cells use an unrelated reduced folate carrier to acquire the necessary folic acid, expression of the folate receptor is restricted to a few cell types. With the exception of kidney, choroid plexus, and placenta, normal tissues express low or nondetectable levels of the folate receptor. However, many malignant tissues, including ovarian, breast, bronchial, and brain cancers express significantly elevated levels of the receptor. Also, it has recently been reported that the folate receptor β, the nonepithelial isoform of the folate receptor, is expressed in active form on activated, but not resting synovial macrophages.

The binding site for the ligand can include receptors for any ligand molecule, or a derivative or analog thereof, capable of preferentially binding to a receptor uniquely expressed or preferentially expressed/presented on the surface of activated macrophages. A surface-presented protein uniquely expressed or preferentially expressed by activated macrophages is a receptor that is either not present or is present at insignificant concentrations on resting macrophages providing a means for preferential detection of activated macrophages. Accordingly, any receptor that is upregulated on activated macrophages compared to resting macrophages, or which is not expressed/presented on the surface of resting macrophages, or any receptor that is not expressed/presented on the surface of resting macrophages in significant amounts could be used for targeting. In one embodiment the site that binds the ligand conjugates used in accordance with the present invention is a vitamin receptor, for example, the folate receptor, which binds folate or an analog or derivative thereof.

In accordance with the invention the ligand conjugates can bind with high affinity to receptors on activated macrophages. The high affinity binding can be inherent to the ligand or the binding affinity can be enhanced by the use of a chemically modified ligand (i.e., an analog or a derivative) or by the particular chemical linkage, in the ligand conjugate, between the ligand and the chromophore or between the ligand and the chemical moiety capable of emitting radiation.

The chemical linkage in the ligand conjugate between the ligand and the chromophore or between the ligand and the chemical moiety can be a direct linkage or can be through an intermediary linker. If present, an intermediary linker can be any biocompatible linker known in the art. Typically, the linker comprises about 1 to about 30 carbon atoms, more typically about 2 to about 20 carbon atoms. Lower molecular weight linkers (i.e., those having an approximate molecular weight of about 30 to about 300) are typically employed. The linkers can be any of those described in U.S. patent application Ser. No. 10/765,336, incorporated herein by reference.

Generally, any manner of forming a complex between the ligand and the chromophore, between the ligand and the chemical moiety capable of emitting radiation, between a linker and the ligand, or between a linker and the chromophore or chemical moiety capable of emitting radiation can be utilized in accordance with the present invention. With or without a linker, the complex can be formed by conjugation of the components of the conjugate, for example, through hydrogen, ionic, or covalent bonds. Covalent bonding of the components of the conjugate can occur, for example, through the formation of amide, ester, disulfide, or imino bonds between acid, aldehyde, hydroxy, amino, sulfhydryl, or hydrazo groups. Also, in accordance with this invention a linker can comprise an indirect means for associating the ligand with the chromophore/chemical moiety, such as by connection through spacer arms or bridging molecules. Both direct and indirect means for association should not prevent the binding of the ligand to the receptor on the activated macrophages for operation of the method of the present invention. Alternatively, the ligand conjugate can be one comprising a liposome wherein the chemical moiety capable of emitting radiation, for example, is contained within a liposome which is itself covalently linked to the activated macrophage-binding ligand.

In the embodiment where the ligand is folic acid, an analog/derivative of folic acid, or any other folate receptor binding molecule, the folate ligand can be conjugated to the chromophore/chemical moiety by an art-recognized procedure that utilizes trifluoroacetic anhydride to prepare γ-esters of folic acid via a pteroyl azide intermediate. This procedure results in the synthesis of a folate ligand, conjugated to the chromophore/chemical moiety only through the γ-carboxy group of the glutamic acid groups of folate. Alternatively, folic acid analogs can be coupled by art-recognized procedures through the α-carboxy moiety of the glutamic acid group or both the α and γ carboxylic acid entities.

The amount of the conjugate effective for use in accordance with the method of the invention depends on many parameters, including the molecular weight of the conjugate, its route of administration, and its tissue distribution. In accordance with the invention an "effective amount" of the ligand conjugate is an amount sufficient to bind to activated macrophages and to be useful in the identification/monitoring of active atherosclerotic plaques. The effective amount of the ligand conjugate to be administered to a patient being evaluated for atherosclerosis can range from about 1 ng/kg to about 10 mg/kg, or from about 10 μg/kg to about 1 mg/kg, or from about 100 μg/kg to about 500 μg/kg.

The ligand conjugate can be administered in one or more doses (e.g., about 1 to about 3 doses) prior to the catheterization or external imaging procedure. The number of doses depends on the molecular weight of the conjugate, its route of administration, and its tissue distribution, among other factors. When used for identification/monitoring of active atherosclerotic plaques, the catheterization or external imaging procedure is typically performed about 1 to about 6 hours post-administration of the ligand conjugate targeted to activated macrophages, but the catheterization or external imaging procedure can be performed at any time post-administration of the ligand conjugate as long as binding of the ligand conjugate to activated macrophages is detectable.

The ligand conjugates administered in accordance with the method of this invention are preferably administered parenterally to the patient being evaluated for atherosclerosis, for example, intravenously, intradermally, subcutaneously, intramuscularly, or intraperitoneally, in combination with a pharmaceutically acceptable carrier. Alternatively, the conjugates can be administered to the patient being evaluated for atherosclerosis by other medically useful procedures such as in an orally available formulation. In accordance with the invention, a "patient being evaluated for artherosclerosis" means any patient suspected of having artherosclerosis, whether symptomatic or not, who would benefit from an evaluation using the method of the present invention.

The conjugates used in accordance with this invention of the formula L-X are used in one aspect of this invention to formulate diagnostic compositions comprising effective amounts of the conjugate and an acceptable carrier therefor. Examples of parenteral dosage forms include aqueous solutions of the conjugate, for example, a solution in isotonic saline, 5% glucose or other well-known pharmaceutically acceptable liquid carriers such as alcohols, glycols, esters and amides. The parenteral compositions for use in accordance with this invention can be in the form of a reconstitutable lyophilizate comprising the one or more doses of the ligand conjugate. Any orally available dosage forms known in the art can also be used.

The activated macrophage-targeted conjugates used for identifying/monitoring disease states mediated by activated macrophages in accordance with this invention are formed to target and, thus, to concentrate the ligand conjugate at the site of activated macrophage populations (i.e., activated macrophages adhering to the luminal endothelial layer of the plaque or activated macrophages present in the lipid-rich core of the plaque) in the patient being evaluated for atherosclerosis.

In one embodiment of the invention active atherosclerotic plaques comprising activated macrophages are identified/monitored in a patient being evaluated for atherosclerosis by administering a conjugate of the formula L-X wherein L comprises a ligand capable of preferentially binding to activated macrophages, compared to resting macrophages, and X comprises a chromophore or a chemical moiety capable of emitting radiation. The inner lining of a patient's blood vessels is thereafter examined with a catheter-based device capable of detecting a localized concentration of the chromophore/chemical moiety conjugated to the ligand bound to activated macrophages, or by an external imaging technique. Any external imaging technique known in the art can be used.

The ligand conjugates are typically administered as a diagnostic composition comprising a ligand conjugate and a pharmaceutically acceptable carrier. The composition is typically formulated for parenteral administration and is administered to the patient in an amount effective to enable detection of the locale of activated macrophages. The nature of the chromophore/chemical moiety component of the ligand conjugate is dictated by the methodology used for catheter-based detection of the active atherosclerotic plaques. Thus, for example, the chromophore can comprise a fluorophore, such as fluorescein, (see PCT publication number WO 01/074382, incorporated herein by reference, for a description of a ligand-fluorophore conjugate) or another chromophore such as an hematoporphyrin, or a derivative thereof, or a Raman enhancing dye or agent, or a long wavelength fluorescent dye with optical properties that allow detection through many layers of tissue. The component of the ligand conjugate used for detection can also be a chemical moiety, such as a chelating moiety and a metal cation, for example, a radionuclide. It should be noted that the method of the present invention can be used for detecting light or radioactivity emitted from ligand conjugates bound both at the surface of atherosclerotic plaques and below the surface.

Such conjugates wherein the group L is folic acid, a folic acid analog/derivative, or another folic acid receptor binding ligand are described in detail in U.S. Pat. No. 5,688,488, incorporated herein by reference. That patent, as well as related U.S. Pat. Nos. 5,416,016 and 5,108,921, each incorporated herein by reference, describe methods and examples for preparing conjugates useful in accordance with the present invention. The present macrophage-targeted ligand conjugates can be prepared and used following general protocols described in those earlier patents.

In the embodiment where the ligand conjugate comprises a chromophore for use in identifying/monitoring active atherosclerotic plaques, the blood vessel walls can be subjected to predetermined conditions to detect locations on the inner linings of blood vessels where the ligand-chromophore conjugates are concentrated (i.e., active atherosclerotic plaques). Such predetermined conditions include any conditions known in the art to be useful for the detection of a chromophore, such as a fluorophore, using a catheter-based device or external imaging technique. For example, the blood vessel walls can be subjected to radiation, in the ultraviolet, visible, or infrared region of the spectrum, from a laser. Catheter-based techniques employing optical fibers for the pulsed or steady state illumination of atherosclerotic plaques with laser radiation of a given wavelength can be used. A signal generated by the fluorescent light emitted by the ligand conjugates is then conveyed by one or more of the optical fibers to the end of the catheter where it can be analyzed to yield information about the atherosclerotic plaque being evaluated. The light emitted can be analyzed using art-recognized techniques as described below to identify/monitor the atherosclerotic plaque being evaluated.

In view of the increase in folate receptor levels during macrophage activation, a ligand conjugate comprising a $^{99m}$Tc chelating chemical moiety targeted to activated macrophages using a vitamin, such as folate, can be used to detect active plaques in vivo. Such a ligand conjugate is described in U.S. Patent Application No. 60/378,571, incorporated herein by reference. Typically the activated macrophage-targeted ligand conjugate is administered to a patient, and following a period of time sufficient (e.g., from about 1 to about 24 hours) for the ligand conjugate to bind to activated macrophages associated with the active plaques, the patient is subjected to the catheterization procedure or an external imaging technique and identification/monitoring of active plaques is enabled by the targeted ligand conjugate.

Active atherosclerotic plaques can be identified/monitored in accordance with the method of the invention by, for example, spectral analysis of fluorescence emitted by the chromophore where the fluorescence emission is stimulated by radiation from, for example, a laser (e.g., laser-induced fluorescence spectroscopy), or by analysis of radioactivity emitted by the chemical moiety. Exemplary analytical techniques are described in U.S. Pat. Nos. 4,718,417 and 4,785,806, and in U.S. Patent Application Publication No. US 2003-0162234 A1, each incorporated herein by reference, but any technique useful for analyzing light or radioactivity emitted from an atherosclerotic plaque to identify/monitor the atherosclerotic plaque in accordance with the invention can be used. In one embodiment, the fluorescence or radioactivity analysis is used to control an ablation laser, and accordingly, the ablation laser is activated, automatically or manually, after the diagnostic laser.

A variety of lasers known in the art can be used in the method of the invention. Exemplary lasers include holmium-doped yttrium aluminum garnet (YAG), holmium-doped yttrium lithium fluoride (YLF), and thulium-doped YAG and thulium-doped YLF. Further details regarding these and other suitable lasers are disclosed in U.S. Pats. Nos. 4,917,084 and 4,950,266, which are hereby incorporated by reference.

The methods described in U.S. Pats. Nos. 5,217,456, 5,275,594, 5,562,100, 6,167,297, 6,217,847, 6,246,901, 6,387,350, 6,507,747, incorporated herein by reference, can also be used to stimulate emission of light from ligand-chromophore conjugates in accordance with the present invention and to detect/analyze light or radioactivity emitted from the ligand conjugates.

The method of the present invention can be used alone or in combination with any other method(s) known in the art for the detection/analysis/ablation of atherosclerotic plaques. For example, the invention can be used in combination with methods to ablate atherosclerotic plaques in cases where active plaques cause narrowing of blood vessels. In such cases, the ligand conjugates of the present invention can be used not only to identify active atherosclerotic plaques as compared to inactive plaques, but also to distinguish between atherosclerotic and normal tissue to help in ablation procedures. Thus, the present invention can be used to analyze both the physiological and the morphological state of atherosclerotic plaques. For example, angioplasty involves the nonsurgical widening of a vessel narrowed by plaque deposition, and laser energy, for example, directed through optical fibers in a catheter-based device, can be used to ablate or partially remove the plaque deposits. Catheter-based devices for ablating plaques using laser energy are described in U.S. Pat. Nos. 4,817,601, 4,850,351, and 4,950,266, incorporated herein by reference.

When laser energy is used to ablate an atherosclerotic plaque, thermal damage to normal tissue is a serious risk because the energy level of radiation emitted from lasers used for ablation of plaque can damage or destroy normal tissue with the possibility of inadvertent perforation of an artery. Accordingly, the ligand conjugates of the present invention can be used to not only identify active atherosclerotic plaques, but to distinguish between atherosclerotic plaques and normal tissue to avert damage to normal tissue during plaque ablation. Pulsed laser emission can also be used whenever continuous laser exposure might damage the tissue.

The method of the present invention can also be used in combination with other techniques for differentiating between atherosclerotic plaques (e.g., fibrous plaque, calcified plaque, and lipid plaque) and normal tissue during plaque ablation. Such techniques include techniques based on analysis of laser-induced calcium photoemission from calcified plaque and laser-induced fluorescence from noncalcified plaque. Other such techniques include the analysis of fluorescence (e.g., laser-induced fluorescence), at selected wavelengths from tissues in an artery, with or without the use of a dye to enhance the contrast between the fluorescence emitted from atherosclerotic plaques and the fluorescence emitted from normal tissue (see U.S. Pat. Nos. 4,641,650, 4,718,417, and 4,785,806, incorporated herein by reference). Other laser-based techniques that can be used in combination with the method of the present invention to differentiate between atherosclerotic plaques and normal tissue include techniques utilizing laser-induced Raman light scattering and laser-induced plasma photoemission. Any other type of technique employing diagnostic and/or ablation lasers known in the art can also be used in combination with the method of the present invention (see U.S. Pat. Nos. 4,817,601 and 4,850,351, incorporated herein by reference).

The method of the present invention can also be used in combination with any other method(s) known in the art for the detection/analysis/ablation of atherosclerotic plaques, including the methods described in U.S. Pat. Nos. 5,217,456, 5,275,594, 5,562,100, 6,167,297, 6,217,847, 6,246,901, 6,387,350, 6,507,747, incorporated herein by reference. Furthermore, the invention can be used to guide the positioning of therapeutic drugs and nucleic acid constructs positioned in the same catheter assembly or a different catheter assembly (see U.S. Patent Application Publication No. US 2002-0192157 A1, incorporated herein by reference).

Example 1

Analysis of EC20 Uptake in the Organs of Atherosclerotic Rabbits

The Watanabe Heritable Hyperlipidemic rabbit model (i.e., a model for atherosclerosis) was used to determine whether binding of a folate-targeted $^{99m}$Tc chelating chemical moiety (EC20; see U.S. Patent Application No. 60/378,571, incorporated herein by reference) could be detected in the arteries of atherosclerotic rabbits. Watanabe rabbits are LDL receptor deficient and, thus, provide a model for hypercholesterolaemia and atherosclerosis.

Watanabe rabbits (2 rabbits each 6 months old) were purchased from HRP-Covance (PA, USA). The rabbits were kept on a folate deficient diet for 3 weeks at which time the biodistribution of EC20 was evaluated. For the EC20 biodistribution studies, each rabbit was administered with 3.4 mCi of $^{99m}$Tc and $7.4 \times 10^{-9}$ moles of EC20 (EC20 in FIG. 1). One rabbit (i.e., control) also received 1000-fold excess of free folic acid (EC20+FF in FIG. 1). The total injection volume for each rabbit was 400 µl via the marginal ear vein. The rabbits were sacrificed 4 hours after injection, and organs were extracted for EC20 biodistribution analysis (i.e., the radioactivity per gram of tissue was measured; see FIG. 1).

The results presented in FIG. 1 show that specific binding of $^{99m}$Tc-EC20, competed by a 1000-fold excess of free folate, was detected in the aortic arch, the inferior vena cava, the superior vena cava, the pulmonary artery, the thoracic aorta, and the abdominal aorta of the Watanabe atherosclerotic rabbits.

Example 2

Materials

Figure 14:
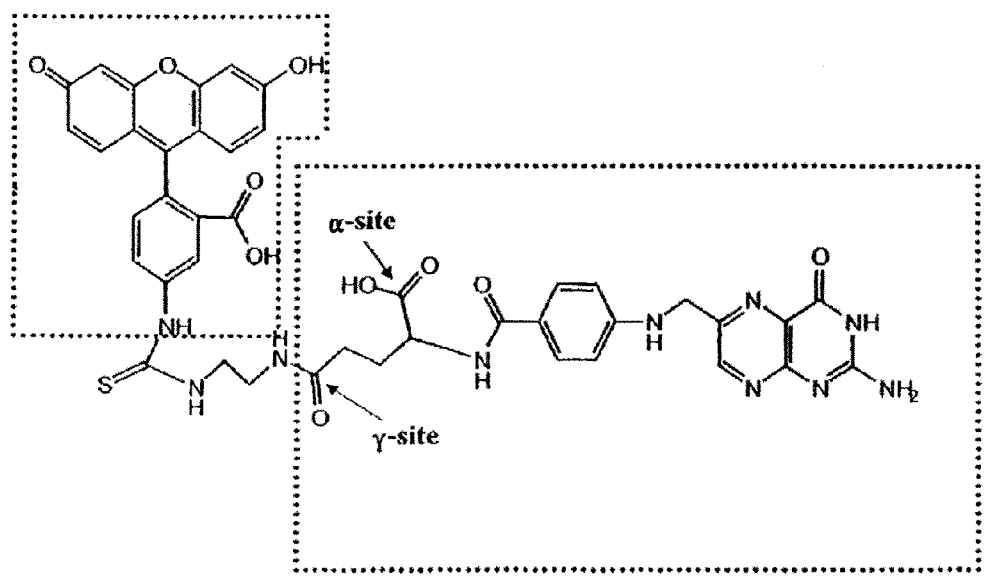
FIG. 14 shows the structure of folate-γ-fluorescein.

Fmoc protected amino acid derivatives, Fmoc-glycine loaded Wang resin, 2-(1H-benzotriazol-1-yl)-1,1,3,3-tetramethyluronium hexafluorophosphate (HBTU) and N-hydroxybenzotriazole were purchased from Novabiochem (San Diego, Calif.). N10-trifluoroacetylpteroic acid was synthesized from folic acid (Sigma Chemical Company, St. Louis, Mo.) according to a previously published report (Godwin, 1972). The synthesis of gamma-carboxy linked folate-fluorescein (folate-FITC) has been described in a previous publication (Kennedy et al., 2003) (FIG. 14). RPMI Medium 1640 with L-glutamine, but without folic acid was from Gibco-BRL (Grand Island, N.Y., U.S.A.); folic acid and triglyceride reagent GPO-PAP were from DIALAB (Vienna, Austria); OCT compound embedding medium for frozen sections were from Division Miles Laboratories Inc. (Illinois, USA); Hoechst 33342 and Texas Red N-hydroxysuccinimide from Molecular Probes, Inc. (Eugene, Oreg., USA); INFINITY CHOLESTEROL reagent and other chemicals were obtained from Sigma Chemical Co. (St. Louis, Mo.).

Example 3

Synthesis of Folate-Texas Red Conjugate

Standard Fmoc peptide chemistry was used to synthesize a folate-derivatized peptide linked to Texas Red via the gamma carboxyl of folic acid. The sequence Gly-Lys-(γ)Glu-pteroic acid was constructed by Fmoc chemistry using HBTU and N-hydroxybenzotriazole as the activating agents along with diisopropylethylamine as the base and 20% piperidine in DMF for deprotection of the Fmoc groups. Fmoc-protected lysine containing a 4-methyltrityl protecting group on the ε-amine was linked to Fmoc-protected glycine attached to a Wang resin. An α-t-Boc protected N-α-Fmoc glutamic acid was then linked to the peptide to provide a γ-linked conjugate on folate after attaching $N^{10}$-trifluoroacetylpteroic acid to the peptide. The methoxytrityl protecting group on the ε-amine of lysine was removed with 1% trifluoroacetic acid in dichloromethane to allow attachment of Texas Red. Texas Red N-hydroxysuccinimide (Molecular Probes, Eugene, Oreg.) in DMF was reacted overnight with the peptide and then washed thoroughly from the peptide resin beads. The folic acid-Texas Red peptide was then cleaved from the resin with 95% trifluoroacetic acid:2.5% water:2.5% triisopropylsilane solution. Diethyl ether was used to precipitate the product and the precipitant was collected by centrifugation. The product was then washed twice with diethyl ether and dried under vacuum overnight. The product was then analyzed and confirmed by mass spectroscopic analysis ([M$^-$] calculated: 1423, found:

1422). In order to remove the $N^{10}$-trifluoracetyl protecting group, the product was dissolved in 5 mls of water containing 0.5 mls of 10% ammonium hydroxide with the pH adjusted to 9.5-10.0 and stirred for 30 minutes at room temperature. The product was then precipitated using isopropanol/ether and the precipitant was collected by centrifugation. The product was then added to a G-10 Sephadex gel filtration column (1.5×15 cm) using water as the eluent. The product peaks were collected and lyophilized.

Example 4

Animal Model

Male healthy RAP mice and Golden Syrian Hamsters were selected for the experiments. Animals were divided in three experimental groups: animals fed with (i) normal diet (N) containing 0.1 g folic acid/100 kg; (ii) folic acid deficient diet (D), and (iii) folic acid deficient diet administered together with hypercholesterolemic food containing 3% cholesterol and 15% butter (H) for 6 months. The folate deficient diet was designed to bring the serum folate levels into the physiologic folate concentration range. Early experiments demonstrated that animals fed with a hyperlipidemic diet and folic acid (0.1 g/100 kg food) developed extensive atherosclerosis; however the specific uptake of folate in these animals could not be measured because of the competition with the high excess of folic acid and the consequent receptor down regulation. Because commercial animal diets are supplemented with supraphysiological concentrations of folic acid, serum folate levels in these "normal" animals will often exceed natural levels by forty-fold (Wang et al.). Such high serum folate contents results in suppression of FR expression.

Example 5

Folate Receptors on Macrophages in Hyperlipidemic Animals

Folic acid conjugated to either FITC (FA-FITC) or to Texas Red (FA-TR) were injected i.p. (10 µg/100 g body weight), and after 4 hours animals were bled (under light ether anesthesia) and then killed by carotid section. A macrophage-enriched suspension (also containing some mast cells, PMN, and monocytes) was then obtained by peritoneal lavage (Aviram, 1989). Briefly, the peritoneal cavity was injected with 10 ml cold phosphate buffered saline (PBS), pH 7.4, and gently massaged for 2 min. The suspension of peritoneal cells was filtered through nylon cloth and washed two times with PBS by centrifugation at 250×g, 10 minutes at 4° C. The pellet was then solubilized in cold lysis buffer (1% NP-40, 50 mM TRIS-HCl, 2 mM EDTA, 1 mM DTT, PMSF, protease inhibitors (leupeptin, antipain, and pepstatin A, 10 µg/ml each)), cleared by centrifugation, and the fluorescence was quantified with a RF-5001 PC spectrophotofluorimeter using a standard curve. Protein concentration was determined by Amido Black and the results were expressed as a ratio of ng FA/mg protein for each group of animals. The same determinations were performed for the serum sample collected from each animal (ng FA-FITC/serum protein). In control experiments animals were injected with the FA-FITC conjugate in the presence of a 100× excess of free folic acid. The total cholesterol and serum triglyceride concentration after six months of diet were measured using specific reagent kits.

Figure 2:
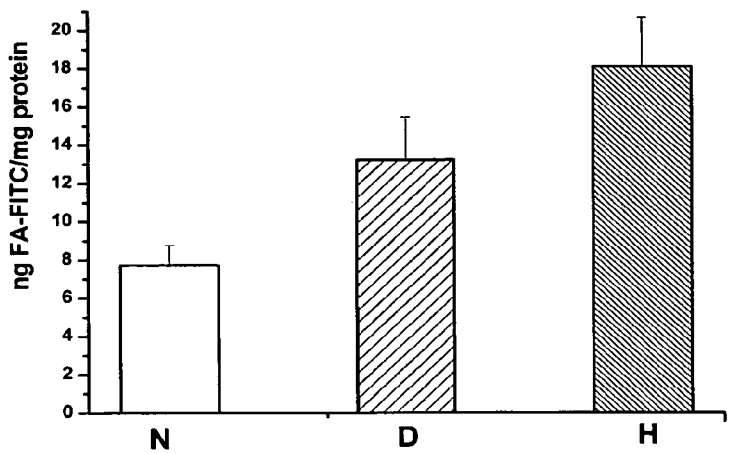
FIG. 2 shows folate-FITC retention by macrophages harvested from hyperlipemic hamsters (H) compared to animals maintained on either normal (high folate) diet (N) or folic acid (FA) deficient diet (D).
Figure 3:
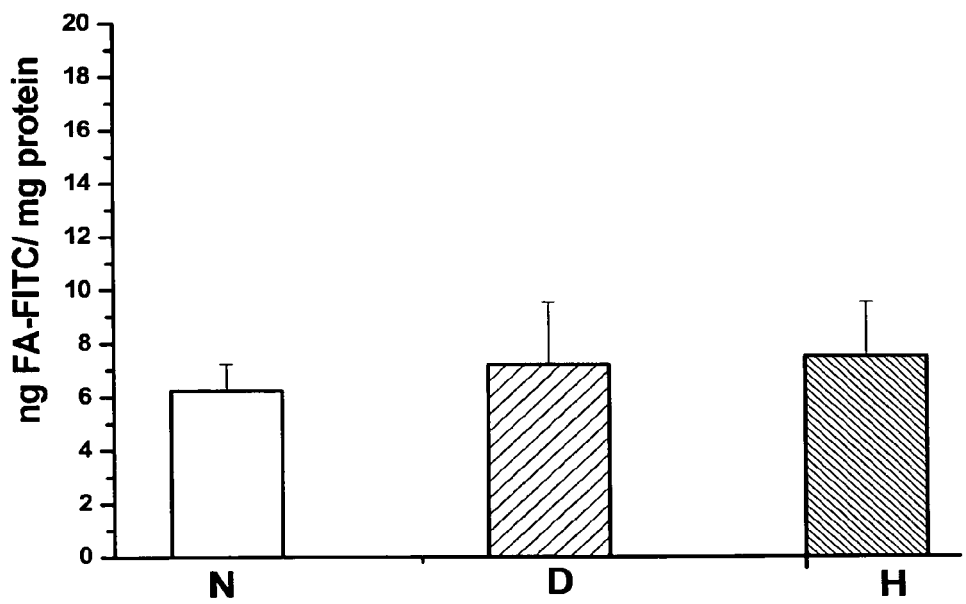
FIG. 3 shows folate-FITC retention by macrophages harvested from hyperlipemic mice (H) compared to animals maintained on either normal (high folate) diet (N) or folic acid (FA) deficient diet (D).
Figure 4:
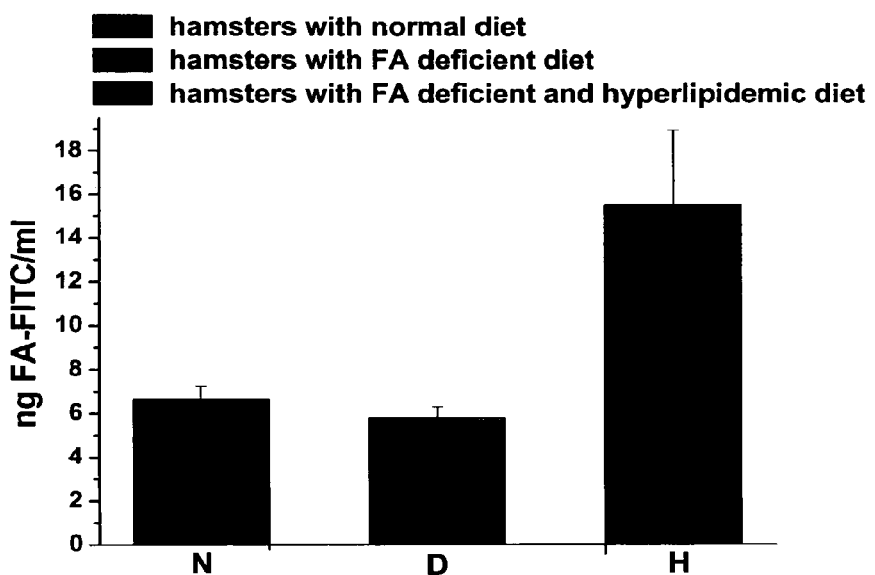
FIG. 4 shows the serum levels of folate-FITC in hyperlipemic hamsters (H) compared to animals maintained on either normal (high folate) diet (N) or folic acid (FA) deficient diet (D).

In order to determine whether peritoneal macrophages from Golden Syrian hamsters express functional folate receptors, folate-FITC was injected into the hamsters intraperitoneally and uptake of the folate conjugate by macrophages extracted 4 hours later was examined by quantitative fluorimetry. The results in FIG. 2 show a significant increase in the folate conjugate's retention by macrophages harvested from hyperlipemic hamsters (H) compared to animals maintained on either normal (high folate) diet (N) or FA deficient diet (D). The folic acid deficient diet induced a significant increase in folate-FITC uptake in both groups D and H, but the folate-FITC levels were 2.4 times higher in macrophages from group H animals (which received hyperlipidemic diet) than controls (N). These data suggest that maintenance of the animals on a folate deficient diet stimulates partial up-regulation of the folate receptor, and that the added exposure of the animals to a high fat/high cholesterol diet further enhances FR expression on peritoneally-derived macrophages. Importantly, the same differences were not detected in macrophages isolated from mice maintained on a similar diet (FIG. 3), a result that may be explained by the fact that mice are resistant to atherosclerosis, in contradistinction to hamsters which develop lesions similar to those of humans (Sima et al. 1990).

Figure 5:
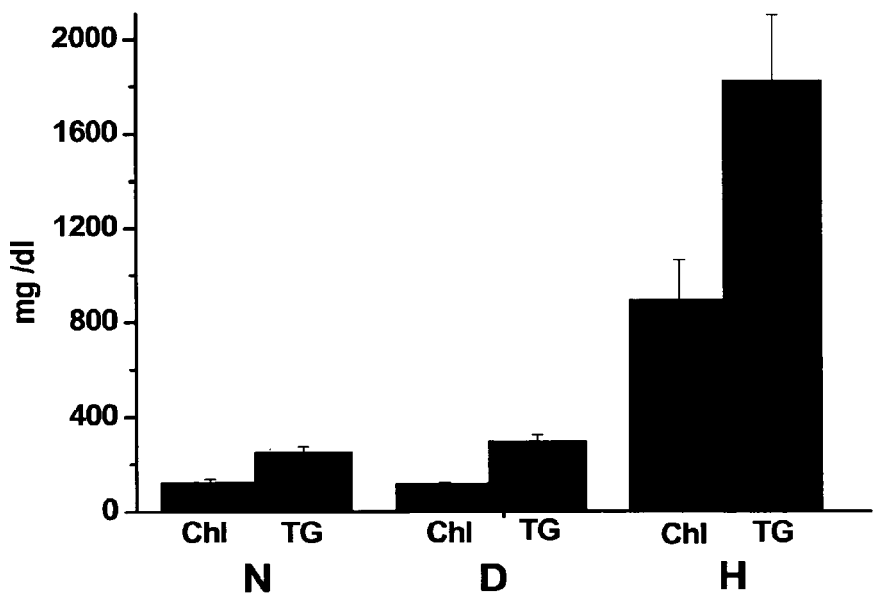
FIG. 5 shows total serum cholesterol and triglyceride levels in hyperlipemic hamsters (H) compared to animals maintained on either normal (high folate) diet (N) or folic acid (FA) deficient diet (D).

In all experimental groups, the serum level of FA-FITC 4 hours post injection was measured. The data indicate a higher concentration of the folate conjugate in serum of hyperlipemic hamsters, suggesting either an acquired deficiency in a clearance mechanism or an increase in folate conjugate binding by serum proteins has occurred in response to the high fat diet (see FIG. 4). The hyperlipidemic condition of the hamsters maintained on the hypercholesterolemic diet was also confirmed by the high level of both total serum cholesterol and triglyceride (FIG. 5). Taken together, the results in FIGS. 2-5 show that the hypercholesterolemic diet induces abnormalities in folate homeostasis, including at least an increase in folate uptake by macrophages and a decrease in clearance of the conjugates from serum.

Example 6

Preparation of Tissue Sections

Tissue fragments from atherosclerotic lesion-prone areas (aorta and valves) were collected from each experimental group and processed for fluorescence microscopy. The aorta was exposed, the branching arteries were cut off, and loose adventitial tissue was removed in situ. The vessel was then cut open and thoroughly washed with cold sterile PBS. Aorta and cardiac valves were carefully excised and all segments were fixed in 4% p-formaldehyde in PBS for 90 min at room temperature. The tissues were then immersed in OTC medium, flash-frozen in liquid nitrogen, and crysectioned. The frozen sections were stained with oil red O and counterstained with hematoxylin (Mancini, 1995). Similar semithin cryosections were examined both in phase contrast and fluorescent microscopy using appropriate filters. Some tissue fragments were processed for standard electron microscopy (Simionescu et al. 1990) in order to visualize the lesion morphology. Thin sections were mordent with uranyl acetate and lead citrate and examined with a Phillips 400 electron microscope.

Figure 6:
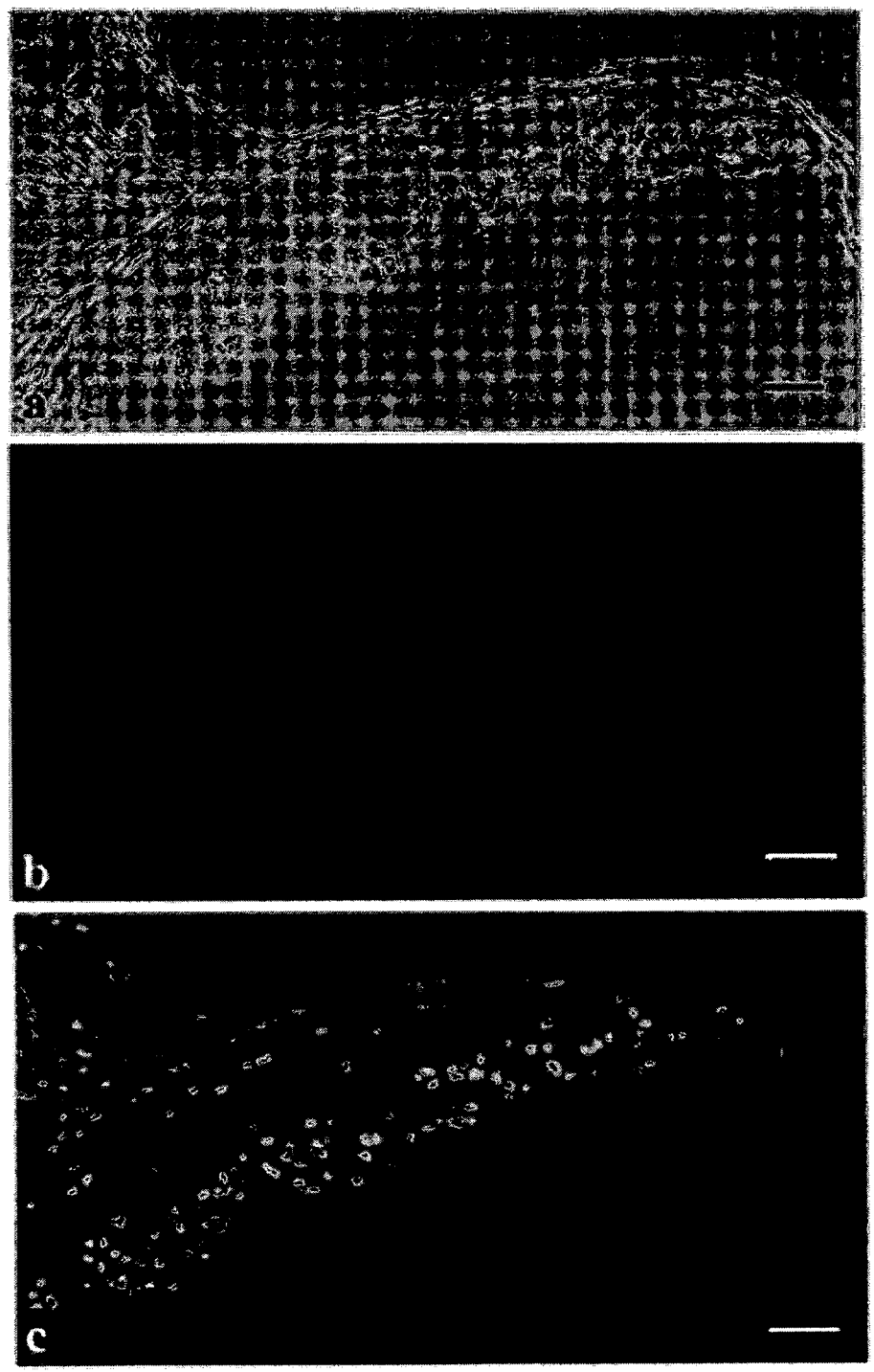
FIGS. 6a, 6b, and 6c show Oil Red staining (FIG. 6a) fluorescence analysis (FIGS. 6b and 6c) of tissue fragments from atherosclerotic lesion-prone areas of Golden Syrian hamsters fed the atherosclerotic diet.
Figure 13:
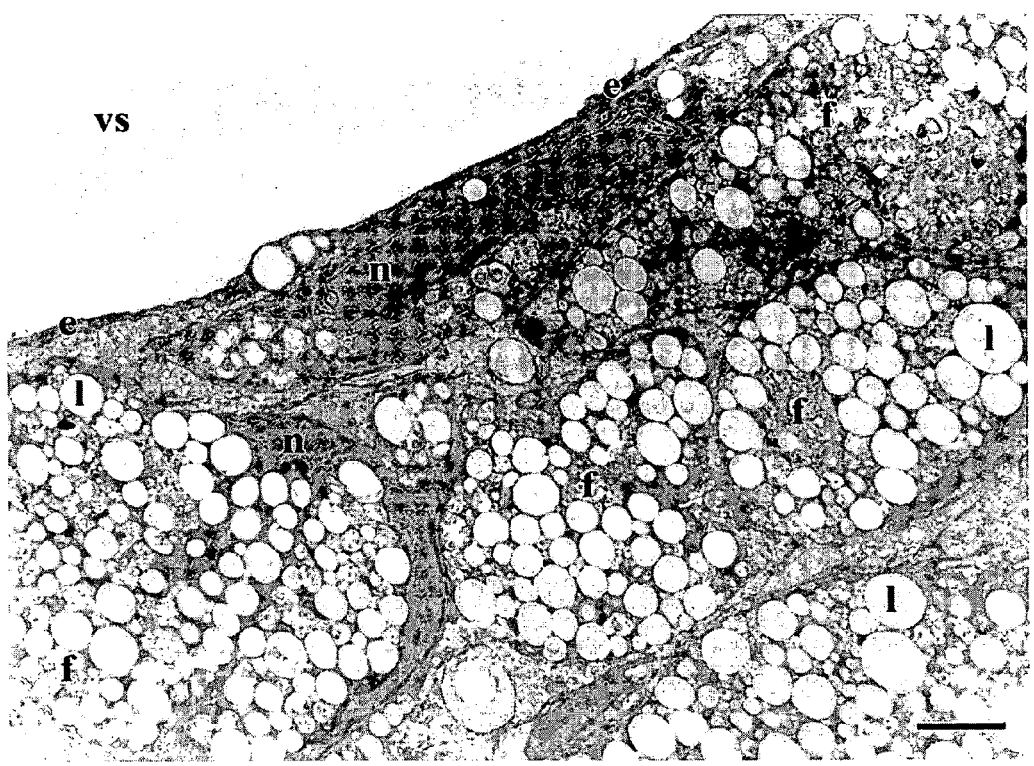
FIG. 13 shows electron micrographs of atherosclerotic lesions on the aortic arch and cardiac valves in hyperlipidemic hamsters.

To determine whether common sites of atherosclerosis might be affected by altered folate homeostasis, 4 hours after i.p. injection of the folate-TR conjugate, tissue fragments from atherosclerotic lesion-prone areas were collected from Golden Syrian hamsters fed on the atherosclerotic diet and processed for fluorescence microscopy. Although animals maintained on either the normal or low folate diet did not develop atherosclerotic lesions and displayed normal serum concentrations of total cholesterol and triglycerides, within 6 months of transfer to the hyperlipidemic diet hamsters developed extensive lesions on both the aorta and cardiac valves (FIG. 13). The lesions displayed a heterogeneous structure and are heavily laden with lipid, as revealed by Oil Red staining of the semithin cryosections (FIG. 6a). Importantly, adjacent unstained sections examined by fluorescence microscopy reveal significant uptake of the folate-Texas Red conjugate, as indicated by the prominent red fluorescence of the fatty lesions (FIG. 6b). Thus, intense FA-TR uptake is seen in distinct foci throughout the atherosclerotic valve (FIG. 6c), while low level FA-TR retention is observed rather uniformly across the fatty lesions. It is possible that the intense fluorescent spots constitute active microdomains where younger activated macrophages are accumulating, whereas the less intensely fluorescent regions may correspond to areas enriched in lipid laden cells (foam cells) that have gradually become more quiescent. The double staining of the sections with Oil Red O (for lipids) and Hoechst (for nucleic acids) confirms clearly that numerous foam cells are tightly packed in the lesion area (FIG. 6c).

Example 7

Specific Uptake of FA-Texas Red in Cultured Peritoneal Macrophages

Hamster peritoneal macrophages ($10-20 \times 10^6$ per hamster) were harvested from peritoneal fluid and washed by centrifugation 3× in PBS at 1000×g for 10 minutes. Cells were suspended in 10 ml of RPMI Medium 1640 containing L-glutamine but lacking folic acid and supplemented with 10% fetal bovine serum (heat inactivated at 56° C. for 30 minutes), 100 U/ml penicillin, and 100 µg/ml streptomycin. Folic acid was left out of the culture medium to the prevent down-regulation of cell surface FR, which usually occurs when cells are cultured in the high folate concentrations present in unmodified RPMI. The peritoneal macrophages were then plated into 50 mm Petri dishes and cultured in a humidified incubator (5% $CO_2$, 95% air). After 2 hours of incubation, the cells were washed to remove non-adherent cells, and further incubated under similar conditions for an additional 18 hours. The cells were briefly washed, mounted with slow fade and examined under a Texas red filter in the fluorescent microscope (Nikon).

Figure 7A:
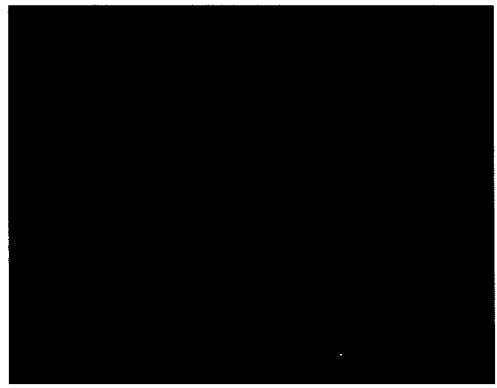
FIGS. 7a and 7b show fluorescence analysis of macrophages harvested from the peritoneum of folic acid-Texas Red treated hypercholesterolemic hamsters.
Figure 7B:
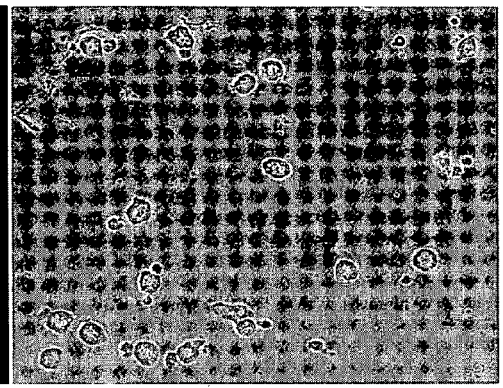

Macrophages harvested from the peritoneum of FA-TR treated hypercholesterolemic hamsters were also found to be significantly more fluorescent (FIG. 7a) than macrophages similarly isolated from animals fed a normal lipid diet, demonstrating that the elevated uptake previously observed for folate-FITC (FIG. 2) can also be replicated using an independent folate conjugate, i.e., FA-TR. Since activated, but not resting macrophages have been reported to express a folate receptor (Nakashima-Matsushita, 1999), the data support the hypothesis that atherosclerosis is an inflammatory disease in which activated macrophages contribute to the development of the plaque.

Example 8

Specific Uptake of FA-FITC in the U937 Cell Line

To extend the study of live animal models, cell culture experiments were also conducted using U937 cells (Harris, 1985), a cell line that originated from the pleural fluid of a patient with diffuse histiocytic lymphoma and which exhibits many characteristics of monocytes. To facilitate their expression of folate receptors, U937 cells were grown in folate-deficient RPMI supplemented with either 5% FCS or with 5% serum from patients with high cholesterol and glucose levels (Chl 295 mg/dl, Glc 315 mg/dl). In parallel experiments aimed at evaluating FR expression following a more classical method of U937 cell activation, U937 cells were incubated in RPMI without folic acid but supplemented with 5% FCS in the presence or absence of 0.5 g/ml bacterial lipopolysaccharide (LPS) or 40 ng/ml phorbol-12 myristate acetate (PMA). After 24 hours of activation either with patient's serum or LPS, cells were incubated with 2.5 g/ml FA-FITC. The cells were then washed with PBS and solubilized in lysis buffer (50 mM Tris-HCl, 1% NP-40, 2 mM EDTA, and 1 mM DTT and protease inhibitors), and FA-FITC uptake was assayed by spectrophotofluorimetry. Protein concentration was determined by BCA methods and the results were expressed as ratio of ng FA-FITC/mg protein for each experimental condition.

Figure 8:
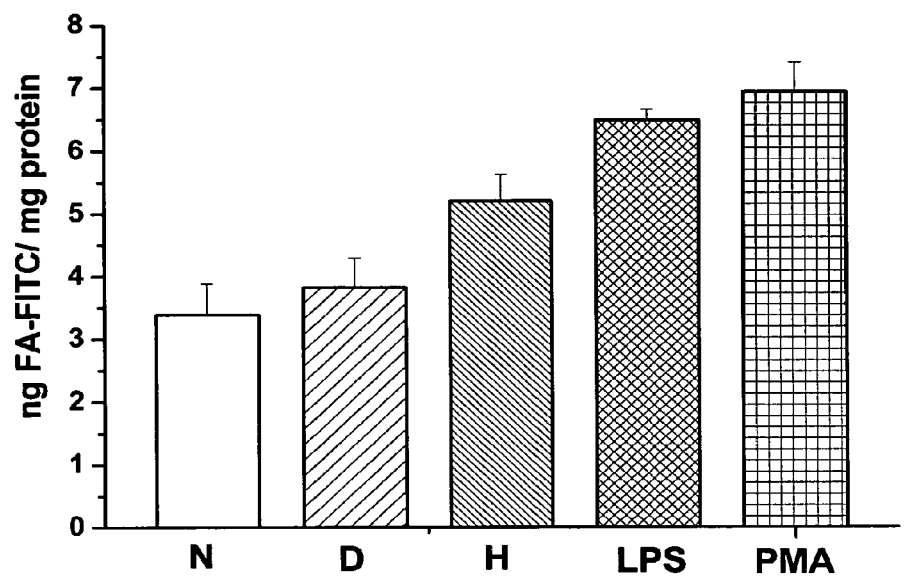
FIG. 8 shows folate-FITC retention by U937 cells grown in either normal medium (N), folic acid deficient medium (D), or hyperlipidemic medium (H) or normal medium supplemented with LPS or PMA.

U937 cells (Sundstrom, 1976), are cells derived from committed progenitors of the monocyte lineage. To detect the stimuli that induce FR up-regulation during macrophage activation, experiments were performed on U937 cells exposed to hyperlipidemic sera, LPS or PMA. In preliminary experiments, it was verified that uptake of FA-FITC by U937 cells is specifically folate receptor mediated by demonstrating that addition of 100-fold excess free folic acid would block uptake of the FA-FITC conjugates. FA-FITC retention by U937 cells grown in either normal (N) medium (RPMI supplemented with 5% fetal calf serum), hyperlipidemic (H) medium (RPMI supplemented with 5% serum from a hypercholesterolemic patient), or in folate deficient RPMI supplemented with 5% fetal calf serum (D), was then evaluated. For comparison, we also examined folate-FITC internalization by U937 cells grown in the same folate deficient RPMI treated with LPS or PMA. As shown in FIG. 8, by the end of the 4 hour incubation, higher FA-FITC uptake (1.6×) was observed in U937 cells grown in medium supplemented with the hyperlipidemic serum (H) than in cells maintained in normal (N) medium (FIG. 8). Interestingly, an even higher level of folate-FITC retention (×2) was obtained when cells were exposed to bacterial lipopolysaccharide (LPS), a ligand known to induce secretion of chemokines responsible for differentiation of U937 cells into cells with characteristics of an activated macrophage (Wang, 1998). A similar increase (×2.1) was observed when the cells were stimulated with the phorbol myristate acetate (PMA), a mimic of diacylglycerol known to activate protein kinase C (Smart et al. 1994). Taken together, these experiments suggest that hypercholesterolemic conditions induce over-expression of folic acid receptors on macrophages, in a manner similar to direct activation of the macrophages by treatment with lipopolysaccharide or PMA.

Example 9

$^{99m}$Tc-Folate SPECT-CT

EC20 was prepared as described in U.S. Patent Application No. 60/378,571, incorporated herein by reference. C57BL/6 male mice were prepared for imaging assays by maintaining the mice for more than 6 months on a high cholesterol and high fat diet of coconut butter (see Paigen et al., *Atherosclerosis*, 57:65-73 (1985), incorporated herein by reference). The mice were rendered diabetic by 6 daily intraperitoneal injections of streptozotocin at a dose of 55 mg/kg.

After 6 months on the high cholesterol and high fat diet, the animals were injected with 10 mCi of $^{99m}$Tc-folate intravenously. After about 5 hours, the animals were anesthetized with isoflurane and microSPECT-CT images of the distribution of $^{99m}$Tc-folate were recorded (see FIGS. 9-11). SPECT-CT was performed with an instrument from Gamma Medica Instruments, Northridge, Calif. SPECT was performed with a 1 mm pinhole collimator using 64 projections and 60 seconds/projection. CT was performed with a project resolution of 128 and a 360 degree rotation.

Figure 9:
FIG. 9 shows a CT, a SPECT, and a SPECT-CT image of a control mouse injected with a folate-targeted $^{99m}$Tc chelating chemical moiety (EC20).
Figure 10:
FIG. 10 shows a CT, a SPECT, and a SPECT-CT image of a mouse maintained on a high cholesterol and high fat diet and then injected with EC20.
Figure 11:
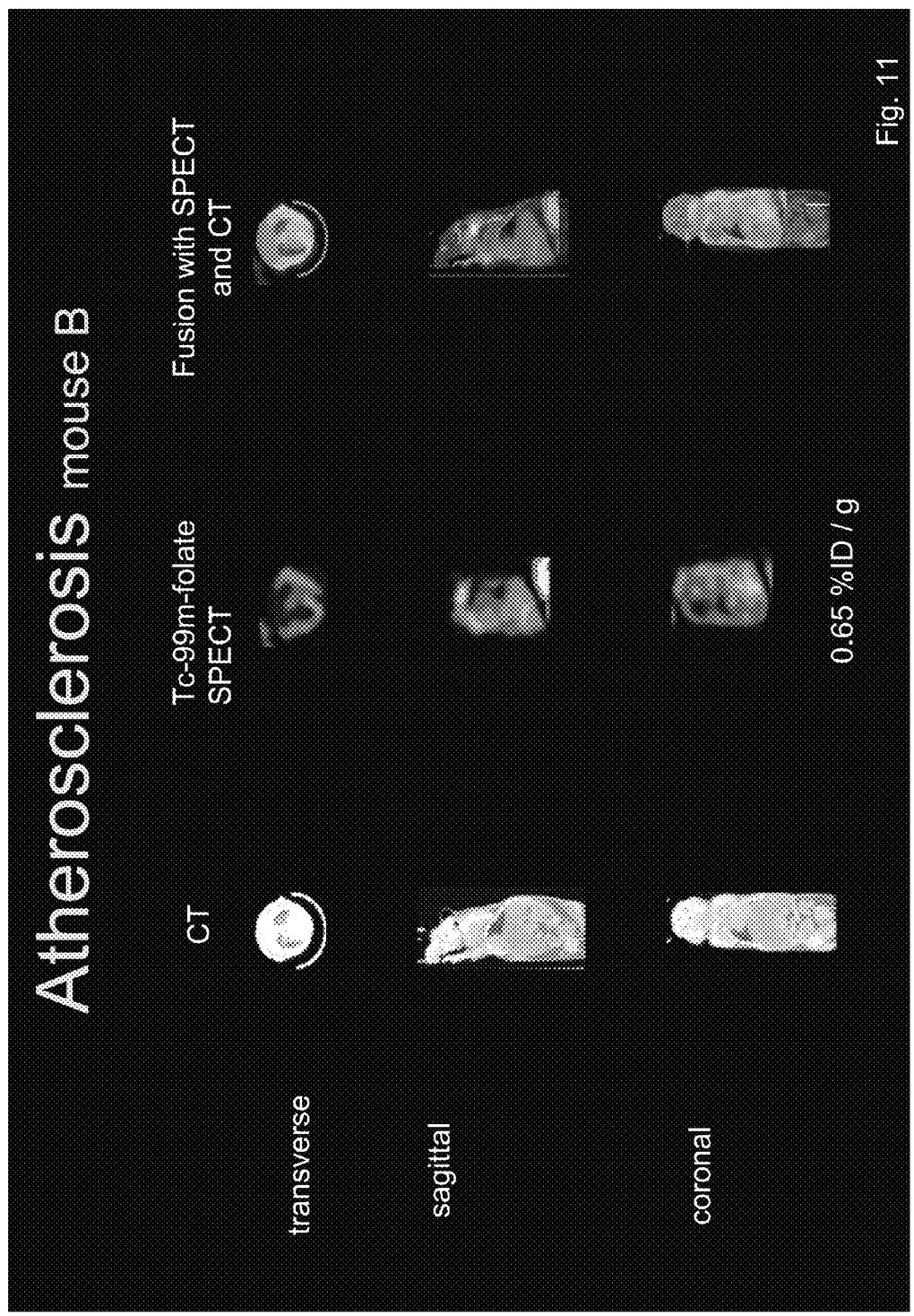
FIG. 11 shows a CT, a SPECT, and a SPECT-CT image of a mouse maintained on a high cholesterol and high fat diet and then injected with EC20.

As shown in FIG. 9 (control mouse) as compared to FIG. 10 (mouse maintained on a high cholesterol and high fat diet), $^{99m}$Tc-folate (EC20) localizes to the heart in atherosclerotic mice and is detectable by microSPECT-CT imaging. In the mouse shown in FIG. 11 localization to the heart was not detectable by microSPECT-CT imaging, likely because the mouse (mouse B) did not develop atherosclerosis that was as severe as mouse A. However, as described in Example 10 below, inflammation and formation of atherosclerotic plaque occurred in mouse B (maintained on a high cholesterol and high fat diet) and the inflammation and plaque is detectable with $^{99m}$Tc-folate (EC20).

Example 10

$^{99m}$Tc-Folate Biodistribution and Autoradiography

Mice were maintained on a high cholesterol and high fat diet as described in Example 9 and were injected with 10 mCi of $^{99m}$Tc-folate intravenously. After microSPECT-CT imaging as described in Example 9, the mice were sacrificed by $CO_2$ asphyxiation. Autoradiography of the aorta and of individual heart slices was performed. The specimens were placed on the autoradiographic plate and exposed for an additional month to record the distribution of $^{99m}$Tc-folate (see FIG. 12 C). Some samples of the mouse hearts were stained with H & E and examined microscopically to confirm the findings of inflammation in atherosclerotic arteries (see FIG. 12 A and B). The results presented in FIG. 12 A-C show that inflammation and formation of atherosclerotic plaque has occurred in mice (mouse B in this case) maintained on a high cholesterol and high fat diet and that the inflammation and plaque is detectable with $^{99m}$Tc-folate (EC20).

The invention claimed is:

1. A method of identifying atherosclerotic plaques associated with blood vessel walls wherein the plaques comprise activated macrophages having folate receptors, said method comprising the steps of:
administering to a patient being evaluated for atherosclerosis an effective amount of a composition comprising folate conjugated to a chromophore wherein the conjugate has the formula

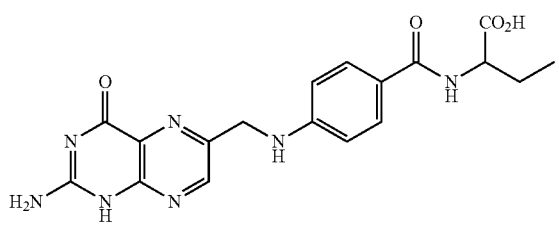

-continued

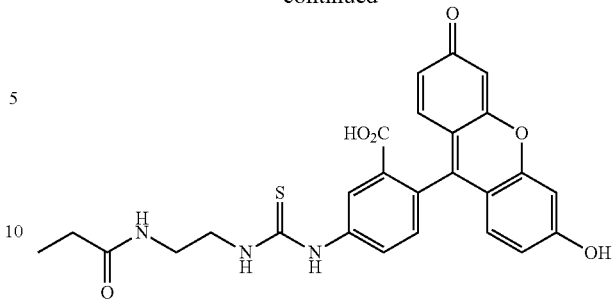

wherein the conjugate exhibits specific binding to the folate receptors;
allowing sufficient time for the conjugate to bind to the activated macrophages associated with the plaques; and
identifying the plaques by detecting light emitted by the chromophore associated with the blood vessel walls using a method selected from the group consisting of the use of a catheter-based device and external imaging.

2. The method of claim 1 wherein the light emitted by the chromophore is detected using a catheter-based device.

3. The method of claim 1 wherein the light emitted by the chromophore is detected using external imaging.

4. The method of claim 1 wherein the composition is in a parenteral dosage form.

5. The method of claim 4 wherein the parenteral dosage form has a route of administration selected from the group consisting of intradermal, subcutaneous, intramuscular, intraperitoneal, and intravenous administration.

6. The method of claim 5 wherein the route of administration is intraperitoneal administration.

7. The method of claim 5 wherein the route of administration is subcutaneous administration.

8. The method of claim 5 wherein the route of administration is intravenous administration.

9. The method of claim 1 wherein the composition comprises a pharmaceutically acceptable carrier.

10. The method of claim 9 wherein the pharmaceutically acceptable carrier is a liquid carrier.

11. The method of claim 10 wherein the liquid carrier is selected from the group consisting of saline, glucose, alcohols, glycols, esters, amides, and a combination thereof.

12. The method of claim 1 wherein the conjugate is administered in one or more doses.

13. The method of claim 1 wherein the effective amount ranges from about 1 ng to about 10 mg per kilogram of body weight.

14. The method of claim 13 wherein the effective amount ranges from about 10 µg to about 1 mg per kilogram of body weight.

15. The method of claim 14 wherein the effective amount ranges from about 100 µg to about 500 µg per kilogram of body weight.

16. The method of claim 2 wherein the plaques are identified using laser radiation.

17. A method of monitoring atherosclerotic plaques associated with blood vessel walls wherein the plaques comprise activated macrophages having folate receptors, said method comprising the steps of:
administering to a patient being evaluated for atherosclerosis an effective amount of a composition comprising folate conjugated to a chromophore wherein the conjugate has the formula

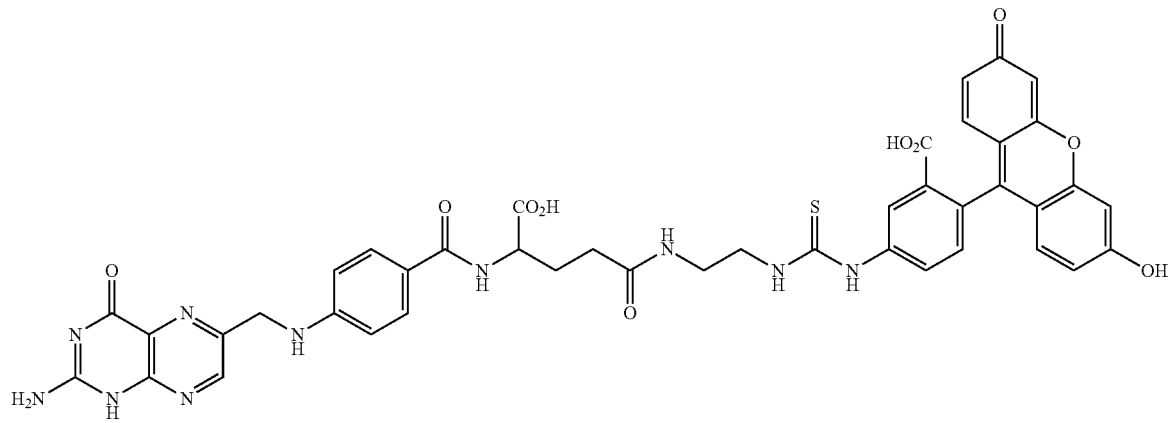 [SMILES: Nc1nc(=O)c2nc(CNc3ccc(C(=O)NC(CCC(=O)NCCNC(=S)Nc4ccc(-c5c6ccc(=O)cc-6oc6cc(O)ccc56)c(C(=O)O)c4)C(=O)O)cc3)cnc2[nH]1]

wherein the conjugate exhibits specific binding to the folate receptors;
allowing sufficient time for the conjugate to bind to the activated macrophages associated with the plaques; and
identifying the plaques by detecting light emitted by the chromophore associated with the blood vessel walls using a method selected from the group consisting of the use of a catheter-based device and external imaging.

18. The method of claim 17 wherein the light emitted by the chromophore is detected using a catheter-based device.

19. The method of claim 17 wherein the light emitted by the chromophore is detected using external imaging.

20. The method of claim 17 wherein the composition is in a parenteral dosage form.

21. The method of claim 20 wherein the parenteral dosage form has a route of administration selected from the group consisting of intradermal, subcutaneous, intramuscular, intraperitoneal, and intravenous administration.

22. The method of claim 21 wherein the route of administration is intraperitoneal administration.

23. The method of claim 21 wherein the route of administration is subcutaneous administration.

24. The method of claim 21 wherein the route of administration is intravenous administration.

25. The method of claim 17 wherein the composition comprises a pharmaceutically acceptable carrier.

26. The method of claim 25 wherein the pharmaceutically acceptable carrier is a liquid carrier.

27. The method of claim 26 wherein the liquid carrier is selected from the group consisting of saline, glucose, alcohols, glycols, esters, amides, and a combination thereof.

28. The method of claim 17 wherein the conjugate is administered in one or more doses.

29. The method of claim 17 wherein the effective amount ranges from about 1 ng to about 10 mg per kilogram of body weight.

30. The method of claim 29 wherein the effective amount ranges from about 10 μg to about 1 mg per kilogram of body weight.

31. The method of claim 30 wherein the effective amount ranges from about 100 μg to about 500 μg per kilogram of body weight.

32. The method of claim 18 wherein the plaques are identified using laser radiation.

* * * * *